US011814670B2

(12) United States Patent
Domanico et al.

(10) Patent No.: US 11,814,670 B2
(45) Date of Patent: *Nov. 14, 2023

(54) MODIFICATION OF DNA ON MAGNETIC BEADS

(71) Applicant: Exact Sciences Corporation, Madison, WI (US)

(72) Inventors: Michael J. Domanico, Middleton, WI (US); Hatim Allawi, Middleton, WI (US); Graham P. Lidgard, Madison, WI (US); Brian Aizenstein, Madison, WI (US); Oliver Hunt, Madison, WI (US); Tobias Charles Zutz, Madison, WI (US)

(73) Assignee: Exact Sciences Corporation, Madison, WI (US)

( * ) Notice: Subject to any disclaimer, the term of this patent is extended or adjusted under 35 U.S.C. 154(b) by 407 days.

This patent is subject to a terminal disclaimer.

(21) Appl. No.: 16/888,397

(22) Filed: May 29, 2020

(65) Prior Publication Data

US 2020/0291459 A1 Sep. 17, 2020

Related U.S. Application Data

(63) Continuation of application No. 16/164,373, filed on Oct. 18, 2018, now Pat. No. 10,704,083, which is a continuation of application No. 15/068,121, filed on Mar. 11, 2016, now Pat. No. 10,144,953, which is a continuation of application No. 13/754,631, filed on Jan. 30, 2013, now Pat. No. 9,315,853.

(60) Provisional application No. 61/592,272, filed on Jan. 30, 2012.

(51) Int. Cl.
*C12Q 1/6806* (2018.01)
*C12Q 1/6851* (2018.01)

(52) U.S. Cl.
CPC ......... *C12Q 1/6806* (2013.01); *C12Q 1/6851* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 4,554,088 A | 11/1985 | Whitehead et al. | |
| 5,647,994 A | 7/1997 | Tuunanen et al. | |
| 5,648,124 A | 7/1997 | Sutor | |
| 5,663,242 A | 9/1997 | Ghosh et al. | |
| 5,702,950 A | 12/1997 | Tajima | |
| 5,786,146 A | 7/1998 | Herman et al. | |
| 6,194,562 B1 | 2/2001 | Smith et al. | |
| 6,270,970 B1 | 8/2001 | Smith et al. | |
| 6,284,470 B1 | 9/2001 | Bitner et al. | |
| 6,296,937 B2 | 10/2001 | Pryor et al. | |
| 6,368,800 B1 | 4/2002 | Smith et al. | |
| 6,376,194 B2 | 4/2002 | Smith et al. | |
| 6,447,729 B1 | 9/2002 | Tuunanen | |
| 6,448,092 B1 | 9/2002 | Tuunanen | |
| 6,613,508 B1 | 9/2003 | Ness et al. | |
| 7,413,855 B2 | 8/2008 | Bergmann et al. | |
| 8,361,720 B2 | 1/2013 | Oldham-Haltom et al. | |
| 8,679,745 B2 | 3/2014 | Ballhause et al. | |
| 9,315,853 B2 | 4/2016 | Domanico et al. | |
| 10,144,953 B2 | 12/2018 | Domanico et al. | |
| 10,704,083 B2* | 7/2020 | Domanico | C12Q 1/6851 |
| 2004/0219695 A1 | 11/2004 | Fox | |
| 2005/0089870 A1 | 4/2005 | Matsubara et al. | |
| 2005/0130172 A1 | 6/2005 | Beard et al. | |
| 2005/0208510 A1 | 9/2005 | Latham et al. | |
| 2006/0204988 A1* | 9/2006 | Fassbender | C12Q 1/6827 435/6.12 |
| 2006/0286577 A1 | 12/2006 | Jia | |
| 2007/0026435 A1 | 2/2007 | Templer et al. | |
| 2007/0178466 A1 | 8/2007 | Hayatsu et al. | |
| 2007/0190530 A1 | 8/2007 | Matsubara et al. | |
| 2008/0281087 A1* | 11/2008 | Markert-Hahn | C12Q 1/6827 536/25.3 |
| 2009/0042290 A1 | 2/2009 | Steele et al. | |
| 2009/0048439 A1 | 2/2009 | Weisburg et al. | |
| 2009/0093378 A1 | 4/2009 | Bignell et al. | |
| 2009/0263909 A1 | 10/2009 | Millar et al. | |
| 2010/0120033 A1 | 5/2010 | Tomigahara et al. | |
| 2011/0003292 A1* | 1/2011 | Dietrich | C12Q 1/6886 435/7.1 |
| 2011/0009277 A1 | 1/2011 | Devos et al. | |
| 2012/0122088 A1 | 5/2012 | Zou et al. | |
| 2012/0122106 A1 | 5/2012 | Zou et al. | |
| 2012/0262260 A1 | 10/2012 | Light, II et al. | |
| 2013/0196322 A1 | 8/2013 | Domanico et al. | |
| 2016/0265033 A1 | 9/2016 | Domanico et al. | |
| 2019/0048399 A1 | 2/2019 | Domanico et al. | |

FOREIGN PATENT DOCUMENTS

| | | |
|---|---|---|
| WO | WO 2005/038051 | 4/2005 |
| WO | WO 2010/118016 | 10/2010 |
| WO | WO 2012/155072 | 11/2012 |

OTHER PUBLICATIONS

Bailey et al., Single-tube analysis of DNA methylation with silica superparamagnetic beads, Clin Chem., 2010, 56:1022-1025.
Callinan et al. "The emerging science of epigenomics," Hum Mol Genet, 2006, 15: R95-101.
CpGenome Universal Methylated DNA, Product Information, 2002-2009, Millipore, 1 page.
Ehrich et al. "A new method for accurate assessment of DNA quality after bisulfite treatment," Nucleic Acids Res, 2007, 35(5):e29.
El-Maarri et al. "Methods: DNA methylation," Adv Exp Med Biol, 2003, 544: 197-204.

(Continued)

*Primary Examiner* — Robert T. Crow
(74) *Attorney, Agent, or Firm* — Casimir Jones, S.C.; Mary Ann D. Brow

(57) ABSTRACT

Provided herein is technology related to the chemical modification and purification of DNA. Specifically, the technology provides methods for performing a bisulfite conversion reaction on small amounts of single-stranded, fragmented DNA and performing the subsequent desulfonation and purification steps on magnetic beads.

13 Claims, 11 Drawing Sheets

(56) References Cited

OTHER PUBLICATIONS

Fraga et al. "DNA methylation: a profile of methods and applications," Biotechniques, 2002, 33(3):632,634, 636-649.
Frommer et al. "A genomic sequencing protocol that yields a positive display of 5-methylcytosine residues in individual DNA strands," Proc Natl Acad Sci USA, 1992, 89: 1827-1831.
Grigg et al., "Sequencing 5-methylcytosine residues in genomic DNA," Bioessays, 1994, 16: 431-436.
Grigg, "Sequencing 5-methylcytosine residues by the bisulphite method," Mitochondrial DNA, 1996, 6: 189-198.
Grunau et al. "Bisulfite genomic sequencing: systematic investigation of critical experimental parameters," Nucl Acids Res, 2001, 29(13): e65-5.
Hayatsu, "Discovery of bisulfite-mediated cytosine conversion to uracil, the key reaction for DNA methylation analysis—a personal account," Proc Jpn Acad Ser B Phys Biol Sci. 2008;84(8):321-330.
Hayatsu et al., "The bisulfite genomic sequencing used in the analysis of epigenetic states, a technique in the emerging environmental genotoxicology research," Mutat Res., 2008, 659:77-82.
Hayatsu et al., "Bisulfite modification for analysis of DNA methylation," Curr Protoc Nucleic Acid Chem, 2008, Ch. 6, Unit 6.10, 15 pages.
Human Genomic DNA, Cat. No. 11 691 112 001, Product Information, Roche Diagnostics GmbH, 2013, 1 page.
Laird et al. "Hairpin-bisulfite PCR: assessing epigenetic methylation patterns on complementary strands of individual DNA molecules," Proc Natl Acad Sci USA, 2004, 101:204-209.
Laird, "The power and the promise of DNA methylation markers," Nat Rev Cancer, 2003, 3(4): 253-266.
Munson et al., Recovery of bisulfite-converted genomic sequences in the methylation-sensitive QPCR, Nucleic Acid Res., 2007, 35:2893-2903.
SiMAG—basic product information, chemicell, retrieved Nov. 7, 2013, 1 page.
Trust Microcon filters for DNA and protein samples, Product Brochure, EMD Milipore, 2012, 2 pages.
Zou et al., Quantification of Methylated Markers with a Multiplex Mehylation-specific Technology. Clin Chem 2012;58(2):375-383.
Zymo Research, EZ DNA Methylation Kit, Instruction Manual, Ver. 1.2.5, zymoresearch.com/downloads/dl/file/id/56/d5001i.pdf, 10 pages, accessed Nov. 18, 2015.
European Supplementary Search Report for EP13743659, dated Aug. 4, 2015, 7 pages.
International Search Report and Written Opinion for PCT Application No. PCT/US2013/023908, dated Apr. 12, 2013.

* cited by examiner

FIG. 8

| NDRG4 | 1 | 2 | 3 | 4 | 5 | 6 | 7 | 8 | 9 | 10 | 11 | 12 |
|---|---|---|---|---|---|---|---|---|---|---|---|---|
| A | 1121 | 480 | 547 | 455 | 488 | 806 | 554 | 529 | 553 | 546 | 589 | 1054 |
| B | 573 | 507 | 438 | 538 | 478 | 695 | 744 | 830 | 964 | 515 | 533 | 547 |
| C | 1007 | 817 | 736 | 594 | 678 | 841 | 875 | 715 | 706 | 815 | 910 | 1105 |
| D | 953 | 1018 | 860 | 801 | 827 | 1014 | 841 | 781 | 891 | 799 | 1343 | 1090 |
| E | 1050 | 1337 | 973 | 981 | 1198 | 800 | 1027 | 884 | 799 | 1054 | 1271 | 1088 |
| F | 1177 | 1308 | 1153 | 1358 | 791 | 915 | 1024 | 1134 | 1028 | 1349 | 1152 | 1135 |
| G | 1263 | 990 | 1185 | 1014 | 1139 | 1124 | 944 | 952 | 1178 | 1277 | 1155 | 1312 |
| H | 1709 | 1496 | 1377 | 1301 | 1468 | 1239 | 1648 | 1194 | 1504 | 1473 | 1499 | 1366 |

FIG. 9

| NDRG4/38A | Methylation NDRG4 | | | | | Mutation 38A | | | |
|---|---|---|---|---|---|---|---|---|---|
| | Te | | | BSA | | Te | | BSA | |
| | 2 | 3 | 4 | 5 | | 8 | 9 | 10 | 11 |
| A | 533 | 777 | 3892 | 4275 | | 20143 | 23362 | 29247 | 30869 |
| B | 972 | 710 | 4360 | 4415 | | 22385 | 22176 | 33166 | 32147 |
| C | 994 | 878 | 4436 | 4822 | | 24827 | 22735 | 27471 | 29478 |
| D | 1075 | 932 | 4320 | 4594 | | 21295 | 22570 | 29559 | 31734 |
| E | 1089 | 1469 | 3833 | 5615 | | 19918 | 21514 | 26408 | 24399 |
| F | 1350 | 1776 | 6820 | 4463 | | 22632 | 23004 | 24715 | 25416 |
| G | 1352 | 1039 | 4901 | 4892 | | 18037 | 20836 | 22618 | 22915 |
| H | 1775 | 2125 | 4176 | 6239 | | 22391 | 22937 | 23499 | 28512 |
| Average strands | 1,178 | | 4,753 | | | 21,924 | | 27,634 | |

FIG. 10

| Ch1 | Methylation Assay - NDRG-4 | | | | | | Mutation Assay- KRAS 38A | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 1863 | 1956 | 2182 | 1484 | 1561 | 1467 | 3841 | 5656 | 5381 | 6031 | 4516 | 4846 |
| B | 1759 | 1888 | 2126 | 1669 | 1962 | 1354 | 3814 | 5616 | 6036 | 5184 | 4156 | 5591 |
| C | 2076 | 1457 | 2092 | 1959 | 1049 | 1761 | 4879 | 6280 | 5589 | 4978 | 3299 | 3539 |
| D | 1967 | 2385 | 2854 | 1998 | 1544 | 1874 | 5156 | 4754 | 5006 | 6159 | 2819 | 5024 |
| E | 2518 | 2702 | 2360 | 1870 | 1477 | 1665 | 5367 | 5691 | 5160 | 5765 | 3562 | 4396 |
| F | 2526 | 2661 | 2761 | 2551 | 2490 | 1991 | 5195 | 5728 | 5151 | 5642 | 4805 | 4840 |
| G | 2252 | 2273 | 2763 | 2812 | 2063 | - | 4864 | 4703 | 5587 | 5463 | 4154 | - |
| H | 2743 | 2586 | 2627 | 2861 | 2531 | - | 5220 | 5472 | 6273 | 5292 | 4122 | - |
| | 5 ng/µL BSA | 10 ng/µL BSA | 10 ng/µL BSA | 10 ng/µL BSA | 20 ng/µL BSA | 20 ng/µL BSA | 5 ng/µL BSA | 10 ng/µL BSA | 10 ng/µL BSA | 10 ng/µL BSA | 20 ng/µL BSA | 20 ng/µL BSA |
| Average strands | 2226 | | 2311 | | 1771 | | 5140 | | 5543 | | 4262 | |

FIG. 11

| | ng/µL casein | Avg Strands | |
|---|---|---|---|
| | | ANB | KRAS |
| FAM | 2.8 | 10,554 | 44,288 |
| | 5.6 | 10,004 | 42,849 |
| | 11.2 | 11,835 | 50,737 |
| HEX | 2.8 | 4,378 | 29,071 |
| | 5.6 | 4,400 | 26,291 |
| | 11.2 | 4,826 | 31,218 |
| QSR | 2.8 | 98,350 | 271,122 |
| | 5.6 | 100,855 | 237,170 |
| | 11.2 | 109,903 | 286,628 |

| | ng/µL BSA | Avg Strands | |
|---|---|---|---|
| | | ANB | KRAS |
| FAM | 28 | 6,960 | 21,460 |
| | 55 | 7,296 | 24,928 |
| | 100 | 6,738 | 31,856 |
| | 200 | 4,383 | 26,150 |
| HEX | 28 | 3,146 | 14,423 |
| | 55 | 3,189 | 18,379 |
| | 100 | 3,443 | 23,000 |
| | 200 | 2,280 | 20,319 |
| QSR | 28 | 64,815 | 120,769 |
| | 55 | 80,171 | 125,977 |
| | 100 | 70,401 | 163,284 |
| | 200 | 56,421 | 143,850 |

MODIFICATION OF DNA ON MAGNETIC BEADS

The present application is a Continuation of U.S. patent application Ser. No. 16/164,373, filed Oct. 18, 2018, now allowed, which is a Continuation of U.S. patent application Ser. No. 15/068,121, filed Mar. 11, 2016, now U.S. Pat. No. 10,144,953, which is a Continuation of U.S. patent application Ser. No. 13/754,631, filed Jan. 30, 2013, now U.S. Pat. No. 9,315,853, which claims priority to U.S. Provisional Application Ser. No. 61/592,272, filed Jan. 30, 2012, each of which is incorporated herein by reference.

FIELD OF INVENTION

Provided herein is technology related to the chemical modification and purification of DNA. Specifically, the technology provides methods for performing a bisulfite conversion reaction on small amounts of single-stranded, fragmented DNA and performing the subsequent desulfonation and purification steps using magnetic beads, and methods of recovering modified DNA from beads.

BACKGROUND

DNA methylation is an epigenetic modification that regulates gene expression and marks imprinted genes. Consequently, aberrant DNA methylation is known to disrupt embryonic development and cell cycle regulation, and it can promote oncogenesis that produces cancers. In mammals, methylation occurs only at cytosine residues and more specifically only on a cytosine residue that is adjacent to a guanine residue (that is, at the sequence CG, often denoted "CpG"). Detecting and mapping sites of DNA methylation are essential steps for understanding epigenetic gene regulation and providing diagnostic tools for identifying cancers and other disease states associated with errors in gene regulation.

Mapping methylation sites is currently accomplished by the bisulfite method described by Frommer, et al. for the detection of 5-methylcytosines in DNA (*Proc. Natl. Acad. Sci. USA* 89: 1827-31 (1992), explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, *Bioessays* (1994) 16: 431-36; Grigg G, *DNA Seq.* (1996) 6: 189-98) or methylation-specific PCR (MSP) as is disclosed, e.g., in U.S. Pat. No. 5,786,146. See also, e.g., Hayatsu, H., Proc. Jpn. Acad., Ser. B 84, No. 8: 321 (2008).

Bisulfite treatment typically requires washing steps and buffer changes to produce a converted and purified DNA sample for analysis. Conventional technologies use a variety of approaches to facilitate these steps, e.g., spin columns, ethanol purification, and solid supports. However, methods using silica spin columns or ethanol purification often result in sample losses that compromise the usefulness of the bisulfite method as a quantitative measure of cytosine methylation. Moreover, though some improvements have been developed using solid supports, these methods require large amounts of DNA as input and also suffer from problems of sample loss and reproducibility. Consequently, conventional methods provide only qualitative measures of DNA methylation. In practice, current methods are generally adapted for sequencing the bisulfite-converted products or for detecting a PCR amplicon only as an end-product, without quantification. Additionally, conventional methods often require long times (e.g., 1-2 days) to complete (e.g., in part due to long incubation times) and do not provide an efficient conversion and recovery of the converted DNA. Methods employing spin columns are labor-intensive and are not readily amenable to automation and thus incorporation into clinical laboratory workflow.

Moreover, conventional bisulfite sequencing often results in the degradation of DNA due to the conditions necessary for complete conversion, such as long incubation times, elevated temperatures, and high bisulfite concentrations. These conditions depurinate DNA, resulting in random strand breaks that can lead to the degradation of 90% of the incubated DNA (see, e.g., Ehrich M, et al. (2007). "A new method for accurate assessment of DNA quality after bisulfite treatment", *Nucleic Acids Res* 35(5): e29; Grunau C, et al. (July 2001), "Bisulfite genomic sequencing: systematic investigation of critical experimental parameters", *Nucleic Acids Res* 29 (13): E65-5). See also, e.g., U.S. Pat. No. 7,413,855. The extensive degradation induced by conventional technologies is problematic, especially for samples containing diminishingly low amounts of DNA. Consequently, downstream analyses (e.g., PCR and other assays) of such samples are severely compromised due to a decreased sampling of representative DNA molecules from the sample. This, in turn, precludes the acquisition of quantitatively accurate information of methylation levels. As such, there is a lack of methods appropriate for the quantitative assessment of the methylation state of small amounts of DNA.

SUMMARY

Accordingly, provided herein is technology related to the modification and purification of DNA. Specifically, the technology provides methods and kits for performing a bisulfite conversion reaction on small amounts of single-stranded, fragmented DNA and performing the subsequent desulfonation and purification steps using magnetic beads for the efficient purification and recovery of the converted DNA. The methods use silica-coated magnetic beads, a stringent high concentration of guanidine hydrochloride in a binding buffer, and a high concentration of ethanol in wash buffers. In preferred embodiments the binding buffer does not include alcohol. The desulfonation and subsequent purification steps are carried out on DNA captured on the beads.

The methods generally proceed as follows. First, the magnetic beads are washed in a binding buffer to remove storage and preservative solution. In a separate reaction, the DNA is subject to bisulfite conversion, e.g., by reaction with a sulfonation reagent such as ammonium hydrogen sulfite (see, e.g., Hayatsu, H., Proc. Jpn. Acad., Ser. B 84, No. 8: 321 (2008)), sodium hydrogen sulfite, or by using a commercial kit. In some embodiments, a high concentration (e.g., a 45% solution) of ammonium hydrogen sulfite is used as a sulfonation reagent. The bisulfite-converted DNA and a binding buffer (e.g., 4.0-8.0 M guanidine hydrochloride, e.g., in some embodiments, approximately 7.0 M guanidine hydrochloride) are added to the beads and incubated to bind the DNA to the beads. In some embodiments, the bead washing and DNA binding steps are combined in a single step in which an excess amount of binding buffer is added to the beads followed by addition of the bisulfite-converted DNA. After binding, the binding solution is removed, the beads are washed, and a desulfonation buffer (e.g., 0.3 N sodium hydroxide in alcohol) is added. The desulfonation buffer is then removed, the beads are washed, and the DNA is eluted in an appropriate DNA elution buffer. The DNA solution is then suitable for a quantitative measurement of bisulfite conversion and thus to provide a quantitative measure of cytosine methylation.

In some embodiments, the desulfonation reagent comprises isopropyl alcohol (isopropanol, 2-propanol, "IPA"), e.g., some embodiments provide a desulfonation reagent that comprises approximately 70% isopropanol and approximately 0.1 N sodium hydroxide.

In some embodiments, the sample vessel in which DNA is captured and washed is exposed to a protein solution, e.g., bovine serum albumin (BSA) and/or casein. For example, in some embodiments, a solution of BSA and/or casein is added the sample vessel containing magnetic beads, e.g., is included in one or more solutions used to process the DNA (e.g., bisulfite conversion, isolation, and/or purification of the DNA) to reduce or eliminate variation in strand recovery. In some embodiments the solution is added to a wash solution used after DNA capture and before elution of the strands. In some embodiments, the sample vessel is wherein said sample vessel is a well of a multi-well plate having, e.g., a plate having 24, 96, 384, or 1536 wells, or any other number of wells. In some embodiments, the methods of the technology are performed in an automated process, e.g., using robotics and or automated liquid handling.

In some embodiments, the technology provided herein provides a method for recovering nucleic acid from a sample vessel, comprising steps of binding nucleic acid in a sample vessel and recovering at least a portion of the nucleic acid from the sample vessel, wherein the sample vessel is exposed to a solution comprising a protein prior to recovering the nucleic acid from the vessel. In some embodiments, the solution comprises at least one of bovine serum albumin or casein. In some embodiments, the nucleic acid is bound to a particle or bead in the sample vessel, e.g., a silica and/or magnetic bead or particle.

In certain preferred embodiments, the protein solution comprises at least 5-10 ng/µl bovine serum albumin, preferably at least 10 ng/µl. In some embodiments, the solution comprises not more than 100 ng/µl bovine serum albumin. In some embodiments, the solution comprises between about 0.001% and about 0.01% casein. In preferred embodiments, the method comprises the recovering of the nucleic acid from the sample well comprises eluting the nucleic acid from a bead or particle in the vessel.

In certain embodiments of the technology, the exposure of the sample vessel to the protein solution occurs after the nucleic acid is bound in the sample vessel, while in other embodiments, the sample vessel is exposed to the solution before the nucleic acid is bound in the vessel. In some embodiments, the nucleic acid is bisulfite treated DNA, and the method comprises desulfonating DNA bound in the sample vessel before the sample vessel is exposed to the protein solution. In other embodiments, the vessel is exposed to the protein prior to desulfonation of the bound DNA.

The technology provides embodiments of the methods for treating DNA comprising contacting a DNA with a bisulfite reagent and binding the DNA to a magnetic bead in a binding buffer. Some embodiments provide additional steps, e.g., washing the DNA with a first wash buffer. Additional embodiments further provide methods comprising contacting the DNA with a desulfonation reagent, washing the DNA with a wash buffer, and eluting the DNA with an elution buffer to produce an analytical sample. In some embodiments, the binding buffer comprises approximately 7 M guanidine hydrochloride and in some embodiments a single wash buffer is used that comprises approximately 80% ethanol and 10 mM Tris HCl at a pH of approximately 8.0.

One aspect of the technology relates to the bisulfite conversion of DNA fragments, e.g., small DNAs of approximately 200 bases or less in length. Accordingly, in some embodiments the DNA subject to bisulfite treatment comprises or consists of a population of DNA strands of 200 or fewer nucleotides in length. Moreover, in some embodiments the DNA is single stranded. Another aspect of the technology provides for the efficient processing and recovery of DNA, e.g., to provide a quantitative measure of cytosine methylation in a sample following a bisulfite reaction. In some embodiments are thus provided methods in which a first amount of DNA in the contacting step is substantially the same as a second amount of DNA in the analytical sample and/or the second amount reflects a near-complete recovery of the first amount after accounting for an appropriate concentration or dilution factor. As a method to treat DNA with bisulfite to convert cytosines, but not methylcytosines, to uracil, some embodiments provide that a cytosine, if present in the DNA, is converted to a uracil. In addition, some embodiments thus provide that a methylcytosine, if present in the DNA, is not converted to a uracil. While the technology is not limited in the types of beads that are used, in some embodiments the magnetic bead is a silica-coated magnetic bead and in some embodiments the bead has a diameter of approximately 1 µm.

Further provided are kits for performing the bisulfite conversion of DNA to quantify the methylation of DNA. In some embodiments, the technology provides embodiments of a kit comprising a sulfonation reagent, a magnetic bead, a binding buffer, a wash buffer, or an elution buffer. In some embodiments of the kits provided, the binding buffer comprises approximately 7 M guanidine hydrochloride and is free of alcohol. In some embodiments, the sulfonation reagent is an ammonium hydrogen sulfite reagent. In some embodiments, the ammonium hydrogen sulfite sulfonation reagent comprises isopropanol.

In some embodiments, it is to be understood that one or more solutions of the kit are to be provided by the user of the kit. For example, in some embodiments a wash buffer is not included in the kit and is supplied by the user of the kit. Kits according to embodiments of the technology comprise a sample tube, an instruction for use, and packaging.

In one aspect, embodiments of the technology provided herein relate to methods of isolating small nucleic acids (e.g., double- or single-stranded DNA consisting of 200 or fewer bases). Such isolation finds use, for example, in the treatment of DNA with bisulfite reagents to quantify DNA methylation. In some embodiments, isolation of small molecules of DNA comprises the use of a DNA binding buffer comprising guanidine hydrochloride and no alcohol. In some embodiments, capture of DNA involves the use of magnetic beads.

Additional embodiments of the technology provided herein will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 3A shows the results of experiments comparing using magnetic beads and a binding buffer as described in the methods, using magnetic beads and using spin columns. Four measurements were performed for each set of conditions. FIG. 3B shows plots of data from a repeat of the experiments that produced the data shown in FIG. 3A.

FIG. 4A shows the results of experiments comparing binding buffers having 4.5 to 8.0 M guanidine hydrochloride without alcohol, and FIG. 4B shows averages of values for replicates in FIG. 4A.

FIG. 5A shows the results of experiments comparing buffers having 5.5 to 7.0 M guanidine hydrochloride without alcohol, and FIG. 5B shows averages of values for replicates in FIG. 5A.

FIG. 8 shows a table comparing the amounts of nucleic acid recovered from 96 replicate wells on a 96 deep-well plate. The recovery of NDRG4 strands from each well of the plate varied as a function of well position, with the general trend of progressively greater recovery from the top (row A) to the bottom (row H) of the plate.

FIG. 9 shows tables comparing the amounts of nucleic acid recovered from replicate wells in which the captured strands were washed with either 10 mM Tris 0.1 mM EDTA ("Te") or a protein solution (BSA) prior to elution.

FIG. 10 shows a table comparing the effects of different concentrations of BSA solution on the average number of strands of NDRG-4 or KRAS-38 synthetic small DNA recovered from a 96-deep well plate, when the assay wells are exposed to the BSA solution prior to elution of the bisulfite-converted DNA. These data are averaged signals for 16 replicate QUARTS assay reactions.

FIG. 11 compares the effects of different concentrations of BSA and casein solutions on the average number of strands of in KRAS and ANB panel synthetic small DNAs recovered from 96 deep-well plates, when the assay wells are exposed to the protein solutions prior to elution of the bisulfite-converted DNA. In the ANB panel, which consists of ACTB ($\beta$-actin, which typically serves as a reference standard in the assays), NDRG4 (member of the N-myc downregulated gene family), and BMP3 (bone morphogenetic protein 3), "FAM" signal indicates the NDRG4 target, "HEX" indicates the BMP3 target, and QSR (Quasar 670) indicates the ACTB target. In the KRAS assays, the FAM signal indicates KRAS 35T, 34T, 38 targets, HEX indicates KRAS 35A, 35C, 34A 34C targets, and QSR indicates ACTB targets. These data are averaged signals for 46 replicate QUARTS assay reactions.

DETAILED DESCRIPTION

Figure 1:
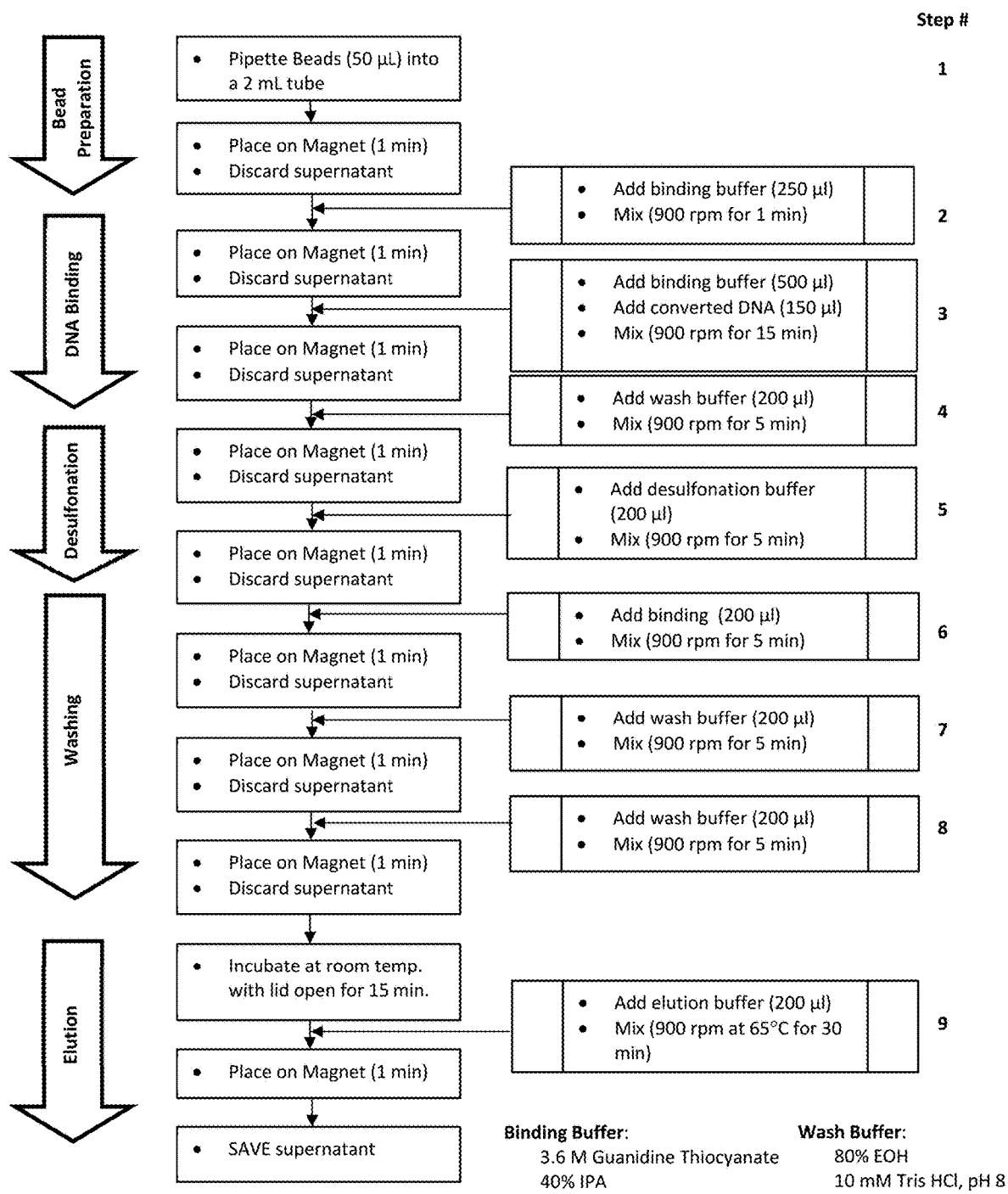
FIG. 1 is a flowchart describing a process for desulfonating bisulfite-treated DNA, in accordance with embodiments of the technology provided herein.

Provided herein is technology related to the chemical modification and purification of DNA. Specifically, the technology provides methods for performing a bisulfite conversion reaction on small amounts of single-stranded, fragmented DNA and performing the subsequent desulfonation and purification steps using magnetic beads. Moreover, the methods provide conditions that promote a highly stable binding of the DNA to the beads. This facilitates the efficient recovery of bisulfite-treated DNA despite the highly basic reaction conditions of desulfonation that one of skill in the art would expect to disrupt the interaction of the DNA with the beads. By combination of the innovative steps provided herein, the technology provides methods for preparing bisulfite-converted DNA quickly, in less than 2 hours, with complete or nearly complete recovery of the input DNA.

The technology is related to the experimental findings described below and developed in the experimental examples. These examples describe the development and testing of reagents used for the analysis of the methylation state of a nucleic acid. In particular, the technology is related to desulfonation buffers comprising isopropanol, alcohol-free binding buffers, and the use of bovine serum albumin and/or casein in various buffers to minimize or eliminate variation in well-to-well strand recoveries when assays are performed in a high-throughput format such as in a 96 deep-well plate. Desulfonation buffers comprising isopropanol solved some problems associated with the use of desulfonation buffers comprising ethanol (e.g., precipitate formation). In addition, assays using binding buffers made without an alcohol produced results with less variability compared to assays using conventional binding buffers comprising an alcohol such as isopropanol or ethanol.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a," "an," and "the" include plural references. Thus, "a" or "an" or "the" can mean one or more than one. For example, "a" widget can mean one widget or a plurality of widgets. The meaning of "in" includes "in" and "on."

As used herein, a "DNA fragment" or "small DNA" or "short DNA" means a DNA that consists of no more than approximately 200 bp. A pol As used herein, the term "genome" refers to the genetic material (e.g., chromosomes) of an organism or a host cell.

As used herein, "sulfonated DNA" refers to the intermediate bisulfite reaction product that is a DNA comprising cytosines or uracils that have been sulfonated as a result of bisulfite treatment.

As used herein, a "small amount" of a DNA means less than about 100,000 molecules of that DNA or one or more DNAs having substantially the same functional sequence.

As used herein, the terms "hydrogen sulfite" and "bisulfite" are interchangeable.

As used herein, the terms "magnetic particles" and "magnetic beads" are used interchangeably and refer to particles or beads that respond to a magnetic field. Typically, magnetic particles comprise materials that have no magnetic field but that form a magnetic dipole when exposed to a magnetic field, e.g., materials capable of being magnetized in the presence of a magnetic field but that are not themselves magnetic in the absence of such a field. The term "magnetic" as used in this context includes materials that are paramagnetic or superparamagnetic materials. The term "magnetic", as used herein, also encompasses temporarily magnetic materials, such as ferromagnetic or ferrimagnetic materials with low Curie temperatures, provided that such temporarily magnetic materials are paramagnetic in the temperature range at which silica magnetic particles containing such materials are used according to the present methods to isolate biological materials.

As used herein, the term "kit" refers to any delivery system for delivering materials. In the context of nucleic acid purification systems and reaction assays, such delivery systems include systems that allow for the storage, transport, or delivery of reagents and devices (e.g., inhibitor adsorbents, particles, denaturants, oligonucleotides, spin filters etc. in the appropriate containers) and/or supporting materials (e.g., buffers, written instructions for performing a procedure, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain materials for sample collection and a buffer, while a second container contains capture oligonucleotides and denaturant. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website.

Embodiments of the Technology

The methods described herein provide for a surprisingly effective and efficient bisulfite conversion of very small amounts of single-stranded DNA fragments, and recovery of the converted product. It was discovered that treatment of DNA fragments using the demethylation protocols described herein, followed by binding the DNA to silica-coated magnetic beads (e.g., as described in U.S. Pat. No. 6,296,937, incorporated herein by reference in its entirety for all purposes, and provided commercially as MAGNESIL Paramagnetic Particles (catalogue number AS1220), Promega, Madison, WI; promega.com) for desulfonation and washing allowed for improved reproducibility (approximately 10% variability), higher DNA yields (approximately 1.10× to 1.25× more yield relative to conventional technologies, e.g., a spin column method), and decreased processing time (approximately 100 minutes) relative to conventional technologies. Some embodiments of these methods comprise use of a stringent binding buffer and a wash buffer comprising 80% ethanol and 10 mM Tris HCl at pH 8. Elution of converted DNA is performed using an elution buffer.

The embodiments described herein find application in nucleic acid from a number of sources, including but not limited to stool samples. Methods of isolating and purifying DNA for use in and with the embodiments described below are found, for example in PCT Patent Publication WO 2012/155072, which is incorporated herein by reference in its entirety, for all purposes.

Additional embodiments of the technology were developed as a result of experiments comprising use of an alcohol-free binding buffer of guanidine hydrochloride. Specific embodiments of the technology are provided below.

Sulfonation of DNA

Experiments conducted during the development of embodiments of the technology provided herein demonstrated that sulfonation of DNA with ammonium bisulfite (ammonium hydrogen sulfite) provides for efficient sulfonation of DNA in a shorter time than sulfonation with sodium bisulfite (sodium hydrogen sulfite). For example, conventional methods for the sulfonation of DNA comprise long, typically overnight, incubations in sodium bisulfite, e.g., for 16 hours or more (see, e.g., Frommer M et al. (1992), "A genomic sequencing protocol that yields a positive display of 5-methylcytosine residues in individual DNA strands" *Proc. Natl. Acad. Sci, USA*. 89:1827-31).

Embodiments of the methods described herein provide for sulfonation of DNA in shorter times (e.g., approximately no more than 1 hour, approximately no more than 2 hours, less than 8 hours, less than 16 hours) by incubation with ammonium bisulfite. Consequently, the technology provided herein reduces the time of the sulfonation reaction and the total time to produce an analytical sample relative to conventional technologies.

Magnetic Beads

The technology provided herein relates to the bisulfite treatment and isolation of DNA for a quantitative measure of DNA methylation. In some embodiments, magnetic beads are used for the treatment and isolation of DNA, e.g., beads comprising a magnetic core and a silica coating. The silica coating binds DNA and the magnetic core provides an efficient way to concentrate and isolate the beads (and bound DNA) using a magnet. In some embodiments, the silica-coated magnetic beads are MAGNESIL Paramagnetic Particles (Promega, Madison, WI; catalogue number AS1220 or AS640A, promega.com).

The technology is not limited to any particular type of magnetic bead. Embodiments of the technology described herein make use of any magnetic beads (e.g., paramagnetic beads) that have an affinity for nucleic acids. In some embodiments, the magnetic beads have a magnetite (e.g., $Fe_3O_4$) core and a coating comprising silicon dioxide ($SiO_2$). The bead structure (e.g., size, porosity, shape) and composition of the solution in which a nucleic acid is bound to the bead can be altered to bind different types (e.g., DNA or RNA in single stranded, double stranded, or other forms or conformations; nucleic acids derived from a natural source, synthesized chemically, synthesized enzymatically (e.g., by PCR)) and sizes of nucleic acids (e.g., small oligomers, primers, genomic, plasmids, fragments (e.g., consisting of 200 or fewer bases) selectively. These characteristics of the beads affect the binding and elution of the nucleic acids to the beads. Related technologies are described, e.g., in U.S. Pat. Nos. 6,194,562; 6,270,970; 6,284,470; 6,368,800; 6,376,194, each incorporated herein by reference. Also contemplated are magnetic beads coated with, e.g., organosilane (as described in U.S. Pat. No. 4,554,088); carboxylated polyacrylate (as described in U.S. Pat. No. 5,648,124); cellulose (as described in U.S. patent application Ser. No. 10/955,974); hydroxysilane (as described in U.S. patent application Ser. No. 11/459,541); and hydrophobic aliphatic ligands (as described in U.S. patent application Ser. No. 12/221,750), each incorporated herein by reference for all purposes.

The technology is not limited to a particular size of magnetic bead. Accordingly, embodiments of the technology use magnetic beads of a number of different sizes. Smaller beads provide more surface area (per weight unit basis) for adsorption, but smaller beads are limited in the amount of magnetic material that can be incorporated in the bead core relative to a larger bead. In some embodiments, the particles are distributed over a range of sizes with a defined average or median size appropriate for the technology for which the beads are used. In some embodiments, the particles are of a relatively narrow monodal particle size distribution.

In some embodiments, the beads that find use in the present technology have pores that are accessible from the exterior of the particle. Such pores have a controlled size range that is sufficiently large to admit a nucleic acid, e.g., a DNA fragment, into the interior of the particle and to bind to the interior surface of the pores. The pores are designed to provide a large surface area that is capable of binding a nucleic acid. Moreover, in one aspect the technology is not limited to any particular method of nucleic acid (e.g., DNA) binding and/or isolation. Thus, in some embodiments, aspects of the technology relating to the bisulfite reaction are combined with other suitable methods of DNA isolation (e.g., precipitation, column chromatography (e.g., a spin column), etc.).

The beads (and bound material) are removed from a mixture using a magnetic field. In some embodiments, other forms of external force in addition to a magnetic field are used to isolate the biological target substance according to the present technology. For example, suitable additional forms of external force include, but are not limited to, gravity filtration, vacuum filtration, and centrifugation.

Embodiments of the technology apply an external magnetic field to remove the complex from the medium. Such a magnetic field can be suitably generated in the medium using any one of a number of different known means. For example, one can position a magnet on the outer surface of a container of a solution containing the beads, causing the particles to migrate through the solution and collect on the inner surface of the container adjacent to the magnet. The magnet can then be held in position on the outer surface of the container such that the particles are held in the container by the magnetic field generated by the magnet, while the solution is decanted out of the container and discarded. A second solution can then be added to the container, and the magnet removed so that the particles migrate into the second solution. Alternatively, a magnetizable probe could be inserted into the solution and the probe magnetized, such that the particles deposit on the end of the probe immersed in the solution. The probe could then be removed from the solution, while remaining magnetized, immersed into a second solution, and the magnetic field discontinued permitting the particles go into the second solution. Commercial sources exist for magnets designed to be used in both types of magnetic removal and transfer techniques described in general terms above. See, e.g., MAGNESPHERE Technology Magnetic Separation Stand or the POLYATRACT Series 9600™ Multi-Magnet, both available from Promega Corporation; MAGNETIGHT Separation Stand (Novagen, Madison, Wis.); or Dynal Magnetic Particle Concentrator (Dynal, Oslo, Norway). Some embodiments comprise use of a magnetic device according to U.S. patent application Ser. No. 13/089,116, which is incorporated herein by reference in its entirety for all purposes. Furthermore, some embodiments contemplate the use of a "jet channel" or pipet tip magnet separation (e.g., as described in U.S. Pat. Nos. 5,647,994 and 5,702,950). Some embodiments contemplate the use of an immersed probe approach (e.g, as described in U.S. Pat. Nos. 6,447,729 and 6,448,092), e.g., as exemplified by the KingFisher systems commercially available from Thermo Scientific.

Alcohol-Free Binding Buffer

Some embodiments relate to the use of an alcohol-free binding buffer. Experiments conducted during the development of embodiments of the technologies described herein demonstrated that an alcohol-free binding buffer (e.g., approximately 6.5-7.5 M guanidine hydrochloride, e.g., 7 M guanidine hydrochloride) performed substantially better than a conventional binding buffer (e.g., approximately 3.6 M guanidine thiocyanate; 10 mM Tris HCl, pH 8.0; 40% 2-propanol). Compare, e.g., Examples 3 and 5 (see, e.g., FIGS. 3A and 3B) with Examples 6 and 7 (FIGS. 4 and 5), each of which used approximately the same quantity of input DNA. The signals achieved using the alcohol-free binding buffer are approximately 1.5 to 2-fold higher than those from the alcohol-containing buffer. The experiments show that recovery of the reaction products using the improved binding buffer provides for a quantitative method of measuring DNA methylation.

The technology contemplates the use of other compositions in the binding buffer, e.g., other salts such as chaotropic salts. Chaotropic salts are salts of chaotropic ions. Such salts are highly soluble in aqueous solutions. The chaotropic ions provided by such salts, at sufficiently high concentration in aqueous solutions of proteins or nucleic acids, cause proteins to unfold, nucleic acids to lose secondary structure or, in the case of double-stranded nucleic acids, melt (e.g., strand-separate). Without being bound by theory, and with an understanding that practice of the technology does not depend on any particular mechanism, it is thought that chaotropic ions have these effects because they disrupt hydrogen-bonding networks that exist in liquid water and thereby make denatured proteins and nucleic acids thermodynamicaily more stable than their correctly folded or structured counterparts. Chaotropic ions include, for example, guanidinium, iodide, perchlorate, and trichloroacetate. In some embodiments, e.g., as described above for the present technology, the salt is a salt of the guanidinium ion. Embodiments of the technology include other salts including guanidine hydrochloride, guanidine thiocyanate (which is sometimes referred to as guanidine isothiocyanate or guanidinium isothiocyanate), sodium iodide, sodium perchlorate, and sodium trichloroacetate. The concentration of salts or chaotropic ions in compositions formed according to the present technologies is generally between about 0.1 M and 8 M and in the embodiments of the technology is sufficiently high to cause the biological target material to adhere to the silica magnetic particles in the mixture, but not so high as to substantially denature, to degrade, or to cause the target material to precipitate out of the mixture.

Isopropanol Desulfonation Buffer

Some embodiments provided herein relate to the use of a desulfonation buffer comprising isopropanol. Experiments conducted during the development of the technologies described herein demonstrated that a desulfonation buffer comprising isopropanol minimized or eliminated some problems associated with the use of desulfonation buffers comprising ethanol. For example, experiments demonstrated that desulfonation buffers comprising ethanol formed precipitates under some conditions. Under the same or similar conditions, desulfonation buffers comprising isopropanol did not form a precipitate. Desulfonation buffers comprising isopropanol find use, e.g., in an automated process where precipitates could compromise the assay of methylation state and/or harm automated equipment performing liquid handling and data collected for the tests.

Solutions Comprising BSA or Casein

Some embodiments provided herein relate to the use of solutions comprising BSA or casein. Experiments conducted during the development of technologies described herein demonstrated that adding BSA or casein to samples minimized or eliminated a variation in strand recovery as a function of well location in a multi-well plate. Moreover, the addition of BSA or casein to samples prior to eluting captured DNA resulted in an increased recovery of strands relative to elutions performed in the absence of BSA or casein. Solutions comprising BSA and/or casein find use in washing or treating the vessel surface prior to use for an assay. The addition of BSA and/or casein was performed, for example, after addition of a high pH elution buffer to the samples and before the addition of a conversion reagent to the samples. Exemplary vessels are, e.g., a vial, a well of a multi-well plate such as a 96 deep-well plate, a tube, etc. Vessels may be made of glass, plastic (e.g., polycarbonate, polystyrene), paper, metal, rubber, etc. In some embodiments, BSA and/or casein is added to wash solutions or other solutions used in embodiments of the methods described herein. For example, after capture and desulfonation of DNA on beads, some embodiments provide for washing the beads, sample vessel, etc. with a solution comprising BSA and/or casein during the purification and/or elution steps of the methods described herein.

In some embodiments, solutions comprising BSA and/or casein and related methods of using BSA and/or casein to treat, manipulate, and/or recover nucleic acids are applied to normalize the recovery of nucleic acid samples in some vessels relative to other vessels (e.g., the individual wells of a 96-well assay plate). For instance, during the development of embodiments of the technology provided herein, the recovery of nucleic acids from a 96-well assay plate varied as a function of well position within the plate. Accordingly, provided herein is technology comprising the use of BSA and/or casein in solutions (e.g., that are added prior to the elution of a nucleic acid) that normalizes the recovery of the nucleic acids from the wells of the 96-well plate (e.g., by increasing the recovery of nucleic acid from wells that would otherwise be reduced in the absence of BSA and/or casein).

Analyzing Bisulfite Reaction Products

In some embodiments, the recovered desulfonated product is analyzed. In some embodiments, the analysis comprises direct sequencing, pyrosequencing, methylation-sensitive single-strand conformation analysis (MS-SSCA), high resolution melting analysis, methylation-sensitive single-nucleotide primer extension (MS-SnuPE), base-specific cleavage/mass spectrometry (e.g., by MALDI-TOF), methylation-specific PCR (MSP), microarray analysis, restriction digest analysis, QUARTS assay (described in U.S. patent application Ser. Nos. 12/946,737; 12/946,745; and Ser. No. 12/946,752, incorporated herein by reference in their entireties for all purposes), INVADER assay, combined bisulfite restriction analysis, or methylated DNA immunoprecipitation (MeDIP). These and other methods are reviewed in more detail in, e.g., Fraga M F & Esteller M (2002), "DNA methylation: a profile of methods and applications", *BioTechniques* 33(3): 632, 634, 636-49; El-Maarri O (2003), "Methods: DNA methylation", *Advances in Experimental Medicine and Biology* 544: 197-204; Laird P W (2003), "The power and the promise of DNA methylation markers", *Nat. Rev. Cancer* 3(4): 253-66; Callinan P A & Feinberg A P (2006), "The emerging science of epigenomics", *Hum Mol Genet* 15(90001): R95-101, which are all incorporated by reference in their entireties for all purposes.

Automation

In one aspect, the technology described herein is amenable to automation, e.g., processing without extensive or any human intervention, e.g., by robotics, computer-control, etc. As such, some embodiments relate to the use of ammonium bisulfite, magnetic beads, alcohol-free binding buffer, isopropanol desulfonation buffer, and/or solutions comprising casein in an automated method or system for processing nucleic acids, e.g., in assays to evaluate the methylation state of a nucleic acid.

Isolation of Small DNA Fragments

Experimental data collected during the development of the technology demonstrated that the technology described provides for the efficient recovery of short DNA molecules from a solution. Accordingly, embodiments of the technology provided herein relate to the purification and quantitative isolation (e.g., greater than 90% recovery, greater than 95% recovery, preferably greater than 97% recovery, and most preferably more than 99% recovery) of small nucleic acid (e.g., DNA) fragments. The technology comprises both the efficient capture of DNA by the beads and the efficient release of the isolated DNA from the beads, both under conditions manipulable by a user of the technology to effect, as desired, binding and release as appropriate for the application. In some embodiments, an alcohol-free binding buffer comprising guanidine hydrochloride finds use in the technology.

SPECIFIC EMBODIMENTS

A specific embodiment of the method, as illustrated in FIG. 1, comprises steps performed as follows. The magnetic beads (e.g., 45-50 µl, e.g., 50 µl) are pipetted into a 2-ml tube, placed on a magnet, and the preservative storage solution is discarded. Then, the beads are suspended and mixed with 200-300 µl (e.g., approximately 250 µl) of binding buffer to wash away any residual storage solution. The binding buffer is then discarded, and bisulfite-converted DNA (e.g., 100-200 µl, e.g., 150 µl) and binding buffer (e.g., 450-550 µl, e.g., 500 µl) are added to the beads and incubated while mixing for 10-20 minutes (e.g., 15 minutes) to allow for the efficient binding of the DNA to the beads. After binding, the beads are placed on a magnet and substantially all of the solution is removed, replaced with approximately 150-250 µl (e.g., 200 µl) of desulfonation buffer, and mixed for 1-10 minutes (e.g., approximately 5 minutes). The desulfonation buffer is then removed by placing the tube on a magnet and removing the supernatant. After this step, the beads are washed once with binding buffer and twice with wash buffer, allowed to dry to remove residual ethanol by evaporation, and then the DNA is eluted from the beads at 60-70° C. (e.g., 65° C.) for 25-35 minutes (e.g., 30 minutes) using a solution comprising approximately 10 mM Tris-HCl, 0.1 mM EDTA, and 20 ng/µl tRNA, at pH 8.0.

Figure 2:
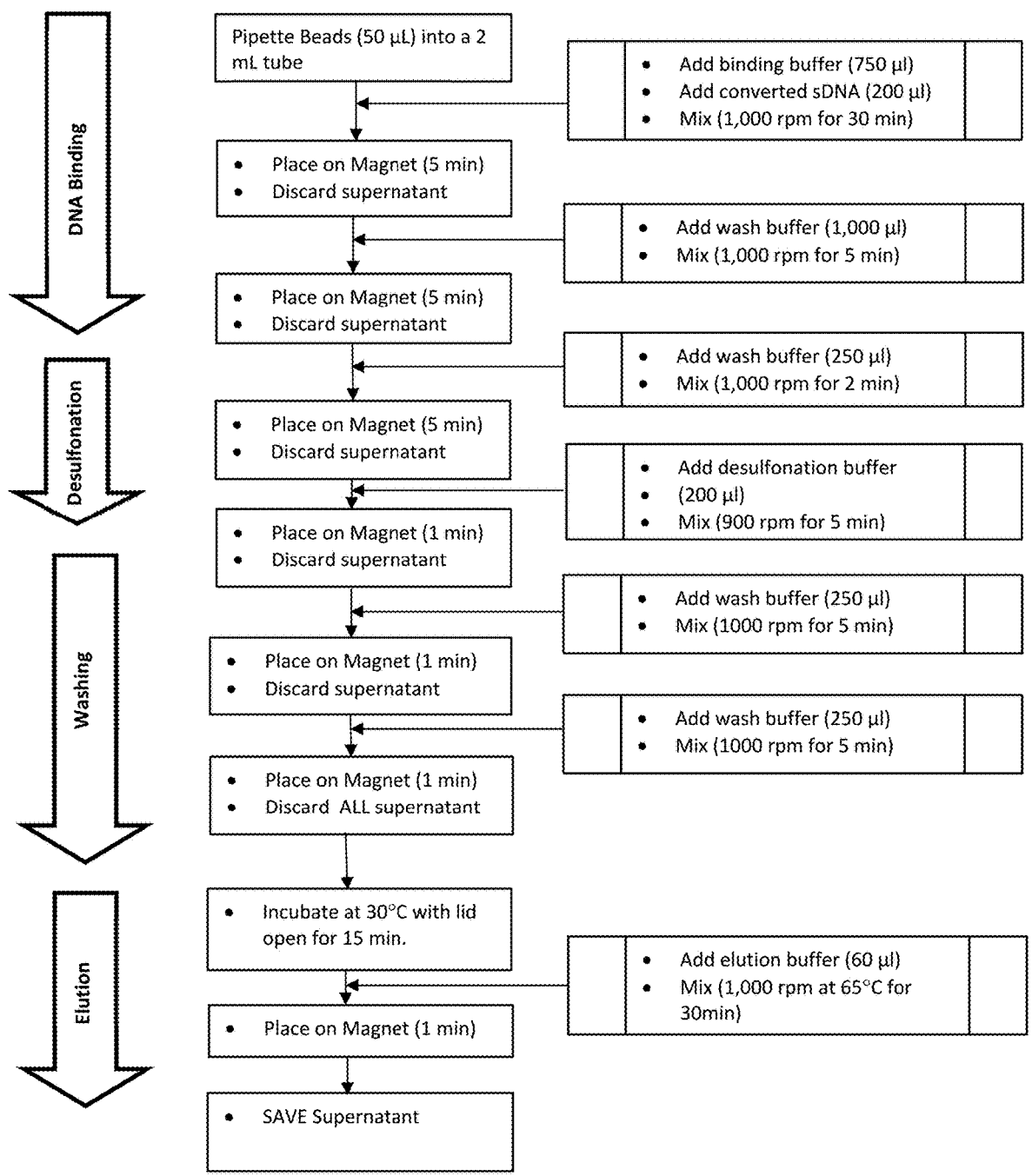
FIG. 2 is a flowchart describing a process for desulfonating bisulfite-treated DNA, in accordance with embodiments of the technology provided herein.

A second specific embodiment is illustrated in FIG. 2. This embodiment provides a method comprising the following steps. First, the magnetic beads (e.g., 45-50 µl, e.g., 50 µl) are pipetted into a 2-ml tube. Then, the beads are mixed with 700-800 µl (e.g., 750 µl) of an alcohol-free binding buffer (e.g., approximately 7 M guanidine hydrochloride) and bisulfite-converted DNA (100-200 µl, e.g., 150 µl). The mixture is incubated with mixing for 25-35 minutes (e.g., approximately 30 minutes) to allow for the efficient binding of the DNA to the beads. After binding, the beads are placed on a magnet and substantially all of the solution is removed, replaced with 900-1100 µl (e.g., 1000 µl) of wash buffer and mixed for 1-10 minutes (e.g., approximately 5 minutes). Then the wash buffer is removed by placing the solution on a magnet and removing the supernatant. Next, 150-250 µl (e.g., 200 µl) of desulfonation buffer is added and mixed for 1-10 minutes (e.g., approximately 5 minutes). The desulfonation buffer is then removed by placing the tube on a magnet and removing the supernatant. After this step, the beads are washed twice with wash buffer (e.g., 80% ethanol; 10 mM Tris HCl, pH 8.0), allowed to dry to remove residual ethanol by evaporation, and then the DNA is eluted from the beads, e.g., by incubation at 25-35° C. (e.g., at approximately 30° C.) for 30-45 minutes using an elution solution (e.g., a solution comprising 10 mM Tris-HCl, 0.1 mM EDTA, and 20 ng/µl tRNA, at pH 8.0).

In some embodiments, one or more solutions used for the processing (e.g., capture wash, capture elution, conversion, and/or purification) of DNA comprises BSA and/or casein to minimize or eliminate a systematic (e.g., top-to-bottom, left-to-right) trending pattern of variation of strand recovery (e.g., up to approximately threefold) as a function of well location (e.g., by column and/or by row) in a multi-well plate (e.g., a 96-well plate, e.g., a deep-well place) and/or to increase strand recovery.

Although the disclosure herein refers to certain illustrated embodiments, it is to be understood that these embodiments are presented by way of example and not by way of limitation. While the detailed description describes the technology as it generally relates to nucleic acids, the detailed description of this particular aspect of the present invention is not intended to limit the scope of the invention. The present disclosure provides sufficient guidance to enable one of ordinary skill in the art of the present invention to use the methods of the present invention to isolate biological target materials other than nucleic acid materials, e.g., proteins or antibodies.

EXPERIMENTAL EXAMPLES

Example 1

Testing Conventional Technology

During the development of embodiments of the technology provided herein, experiments demonstrated that desulfonation and purification of sulfonated DNA using magnetic beads (Promega MAGNESIL Paramagnetic Particles, Promega catalogue number AS1050) and standard reaction conditions recommended by the commercial supplier (binding buffer: 3 M guanidine thiocyanate and 50% isopropyl alcohol; wash buffer 1: 3 M guanidine thiocyanate and 40% isopropyl alcohol; wash buffer 2: 25% ethanol, 25% isopropyl alcohol, and 0.1 M NaCl) resulted in highly variable recovery of processed samples when tested by several users on the same day or different days.

Example 2

Testing Different Types of Magnetic Beads

During the development of embodiments of the technology provided herein, a different type of beads was used to test if reproducibility and recovery would improve. For these experiments, Agencourt RNACLEAN XP magnetic beads were used (Beckman Coulter Genomics, catalogue number A63987). Desulfonation and purification of bisulfite-reacted DNA using these beads resulted in lesser variability than using the MAGNESIL Paramagnetic Particles (Promega, Madison, WI) under the conditions of Example 1, but the beads produced a poor recovery (e.g., a greater than 50-70% loss of DNA).

Example 3

Testing Different Buffer Stringencies

During the development of embodiments of the technology provided herein, the silica-coated magnetic beads used in Example 1 were retested using a modified and more stringent binding buffer comprising 3.6 M guanidine thiocyanate and 50% isopropyl alcohol, an initial wash buffer comprising 3 M guanidine thiocyanate and 50% isopropyl alcohol, and a last step wash buffer comprising 80% ethanol and 10 mM Tris-HCl at pH 8. Use of this protocol resulted in a recovery that was greater than 110% compared to the conventional spin-column method and yielded more reproducible intra- and inter-experiment data.

Example 4

Testing Methods with Fewer Steps and Decreased Processing Time

During the development of embodiments of the technology provided herein, the silica-coated magnetic beads protocol of Example 3 was modified to lessen the amount of time required for satisfactory performance (e.g., considering reproducibility, efficiency, and recovery). Initially, the protocol required 2.5 hours to complete. After decreasing the number of final wash steps from three to two, this showed no effect on the recovery of DNA. Then, wash buffer 1 was combined with the binding buffer, and it was found that use of this modified binding buffer minimally affected the DNA recovery and reproducibility. Various binding and elution times and temperatures were also tried. Experiments showed that lowering the elution temperature from 85° C. to 65° C. and incubating for 20 minutes and decreasing the binding time from 30 to 15 minutes resulted in satisfactory recovery of DNA with less than two hours of total processing time.

Example 5

Testing Desulfonation on Magnetic Beads

During the development of embodiments of the technology disclosed herein, experiments were performed to compare desulfonation on magnetic beads to desulfonation using a spin column.

Materials

Binding buffer: 3.6 M guanidine thiocyanate, 10 mM Tris HCl (pH 8.0), 39% isopropyl alcohol. For example, to make 20 ml of binding buffer, mix 12 milliliters of 6 M guanidine thiocyanate, 0.2 milliliter of 1 M Tris HCl (pH 8.0), and 7.8 milliliters of isopropyl alcohol (2-propanol).

Wash buffer: 80% ethanol with 10 mM Tris HCl (pH 8.0). For example, to make 10 milliliters of wash buffer, mix 8 milliliters of 100% ethanol, 0.1 milliliters of 1 M Tris HCl (pH 8.0), and 1.9 water (double distilled).

Desulfonation buffer: 0.3 N NaOH in ethanol. For example, to make 10 milliliters, mix 7 milliliters of 100% ethanol with 3 milliliters of 1 N sodium hydroxide (NaOH).

Samples are mixed using any appropriate device or technology to mix or incubate samples at the temperatures and mixing speeds essentially as described below. For example, a THERMOMIXER temperature-controlled mixer (Eppendorf) can be used for the mixing or incubation of samples. As used herein, "ANB" refers to an assay of the three markers ACTB (beta actin), NDRG4, and BMP3.

Methods

Ammonium hydrogen sulfite conversion
1. In each tube, combine 10 µl DNA, 4.5 µl N NaOH, and 0.5 µl water (e.g., Fisher 0.1-µm filtered, molecular biology quality)
2. Incubate at 42° C. for 20 minutes.
3. Add 135 µl of 45% ammonium hydrogen sulfite and incubate at 66° for 1 hour.
4. Incubate at 4° C. for 10 minutes.

Desulfonation using magnetic beads
1. Mix bead stock thoroughly by vortexing bottle for 1 minute.
2. Aliquot 50 µl of beads into a 2.0-ml tube (e.g., from USA Scientific).
3. Add 750 µl of binding buffer to the beads.
4. Add 150 µl of sulfonated DNA.
5. Mix (e.g., 1000 RPM at 30° C. for 30 minutes).
6. Place tube on the magnet stand and leave in place for 5 minutes. With the tubes on the stand, remove and discard the supernatant.
7. Add 1,000 µl of wash buffer. Mix (e.g., 1000 RPM at 30° C. for 3 minutes).
8. Place tube on the magnet stand and leave in place for 5 minutes. With the tubes on the stand, remove and discard the supernatant.
9. Add 250 µl of wash buffer. Mix (e.g., 1000 RPM at 30° C. for 3 minutes).
10. Place tube on magnetic rack; remove and discard supernatant after 1 minute.
11. Add 200 µl of desulfonation buffer. Mix (e.g., 1000 RPM at 30° C. for 5 minutes).
12. Place tube on magnetic rack; remove and discard supernatant after 1 minute.
13. Add 250 µl of wash buffer. Mix (e.g., 1000 RPM at 30° C. for 3 minutes).
14. Place tube on magnetic rack; remove and discard supernatant after 1 minute.
15. Add 250 µl of wash buffer to the tube. Mix (e.g., 1000 RPM at 30° C. for 3 minutes).
16. Place tube on magnetic rack; remove and discard supernatant after 1 minute.
17. Incubate all tubes at 30° C. with the lid open for 15 minutes.
18. Remove tube from magnetic rack and add 60 µl of elution buffer directly to the beads.
19. Incubate the beads with elution-buffer (e.g., 1000 RPM at 40° C. for 45 minutes).
20. Place tubes on magnetic rack; remove and save the supernatant after 1 minute.

The DNA is ready for immediate analysis or can be stored frozen (e.g., at or below −20° C.) for later use. For long term storage, store at or below −70° C.

Desulfonation Using a Spin Column

Zymo IC spin columns (Zymo Research, Irvine, CA) were used according to the manufacturer's instructions as follows:
1. Add 400 µl of binding buffer to a ZYMO-SPIN IC Column and place the column into a provided Collection Tube.
2. Load 150 µl the sample into the ZYMO-SPIN IC Column containing the binding buffer. Close the cap and mix by inversion.
3. Centrifuge at full speed for 30 seconds. Discard the flow-through.
4. Add 100 µl of Zymo M-Wash Buffer to the column. Centrifuge at full speed for 30 seconds. Discard the flow-through.
5. Add 200 µl of Zymo M-Desulfonation Buffer to the column and let stand at ambient temperature for 15 minutes.
6. Centrifuge at full speed for 30 seconds. Discard the flow-through.
7. Add 200 µl of Zymo M-Wash Buffer to the column. Centrifuge at full speed for 30 seconds. Discard the flow through.
8. Add 200 µl of Zymo M-Wash Buffer to the column. Centrifuge at full speed for 60 seconds. Discard the flow-through.
9. Place the column into a 1.5-ml microcentrifuge tube. Add 60 µl of Elution Buffer directly onto the column matrix.
10. Centrifuge at full speed for 30 seconds. Save the flow-through containing the sample.

The DNA is ready for immediate analysis or can be stored frozen (e.g., at or below −20° C.) for later use. For long term storage, store at or below −70° C.

QuARTS® Assay

The QUARTS technology combines a polymerase-based target DNA amplification process with an invasive cleavage-based signal amplification process. The technology is described, e.g., in U.S. Pat. No. 8,361,720, and U.S. patent application Ser. Nos. 12/946,745; 12/946,752, and 61/705,603, incorporated herein by reference. Fluorescence signal generated by the QUARTS assay reaction is monitored in a fashion similar to real-time PCR and permits quantitation of the amount of a target nucleic acid in a sample.

An exemplary QUARTS assay reaction typically comprises approximately 400-600 nmol/l (e.g., 500 nmol/l) of each primer and detection probe, approximately 100 nmol/l of the invasive oligonucleotide, approximately 600-700 nmol/l of each FAM (e.g., as supplied commercially by Hologic, Inc.), HEX (e.g., as supplied commercially by BioSearch Technologies, IDT), and Quasar 670 (e.g., as supplied commercially by BioSearch Technologies) FRET cassettes, 6.675 ng/µl FEN-1 (e.g., Cleavase® enzyme (e.g., 2.0), Hologic, Inc.), 1 unit Taq DNA polymerase in a 30 µl reaction volume (e.g., GoTaq® DNA polymerase, Promega Corp., Madison, WI), 10 mmol/l 3-(n-morpholino) propanesulfonic acid (MOPS), 7.5 mmol/l $MgCl_2$, and 250 µmol/l of each dNTP. Exemplary QUARTS assay cycling conditions consist of an initial incubation at 95° C. for 3 minutes, followed by 10 cycles of 95° C. for 20 seconds, 67° C. for 30 seconds, and 70° C. for 30 seconds. After completion of the 10 cycles, an additional 37 cycles at 95° C. for 20 seconds, 53° C. for 1 minute, 70° C. for 30 seconds, and 40° C. for 30 seconds are typically performed. In some applications, analysis of the quantification cycle ($C_q$) provides a measure of the initial number of target DNA strands (e.g., copy number) in the sample.

Reactions are assembled as follows:
1. Vortex 3× Reaction Mix and 3×ANB Oligo Mix for 3-5 seconds. Centrifuge each tube for 1-3 seconds.
2. Formulate the Master Mix in a 2.0-ml tube (e.g., USA Scientific) using 10 µl 3× reaction buffer and 10 µl 3×ANB oligo mix per reaction.
3. Vortex the Master Mix for 3-5 seconds. Centrifuge briefly to collect the sample.
4. Aliquot 50 µl of the Master Mix into 8-well 200-µl tube strips, one for standards and one or more for samples.
5. Vortex and centrifuge the standards and samples. Dispense 25 µl into 200-µl strip tubes containing Master Mix.
6. Cap strip tubes and vortex well. Spin briefly to collect the sample.
7. Add 30 µl of strip tube contents to a LIGHTCYCLER LC480 plate (according to plate layout).
8. Seal plate with LIGHTCYCLER LC480 sealing foil. Centrifuge at 3000 rpm for 2 minutes.
9. After centrifugation, place in LIGHTCYCLER LC480 instrument with the following cycling conditions and begin the assay:

| QUARTS Assay Reaction Parameters | | | | |
| --- | --- | --- | --- | --- |
| Stage | Temp/Time | Ramp Rate (° C. per second) | # of Cycles | Acquisition |
| Pre-incubation | 95° C./3' | 4.4 | 1 | none |
| Amplification 1 | 95° C./20" | 4.4 | 10 | none |
|  | 64° C./30" | 2.2 |  | none |
|  | 70° C./30" | 4.4 |  | none |
| Amplification 2 | 95° C./20" | 4.4 | 35 | none |
|  | 53° C./1' | 2.2 |  | single |
|  | 70° C./30" | 4.4 |  | none |
| Cooling | 40° C./30" | 2.2 | 1 | none |

Figure 3A:
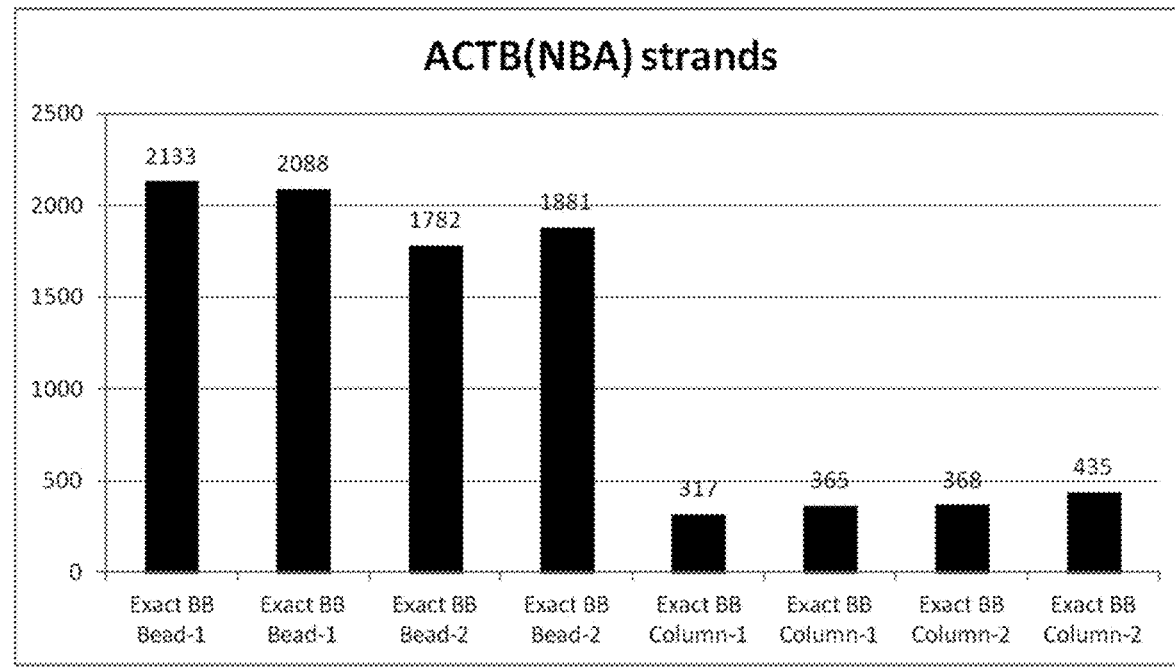
FIGS. 3A-B shows plots of data from experiments comparing the quantitative measurement of DNA methylation as determined by two different protocols.
Figure 3B:
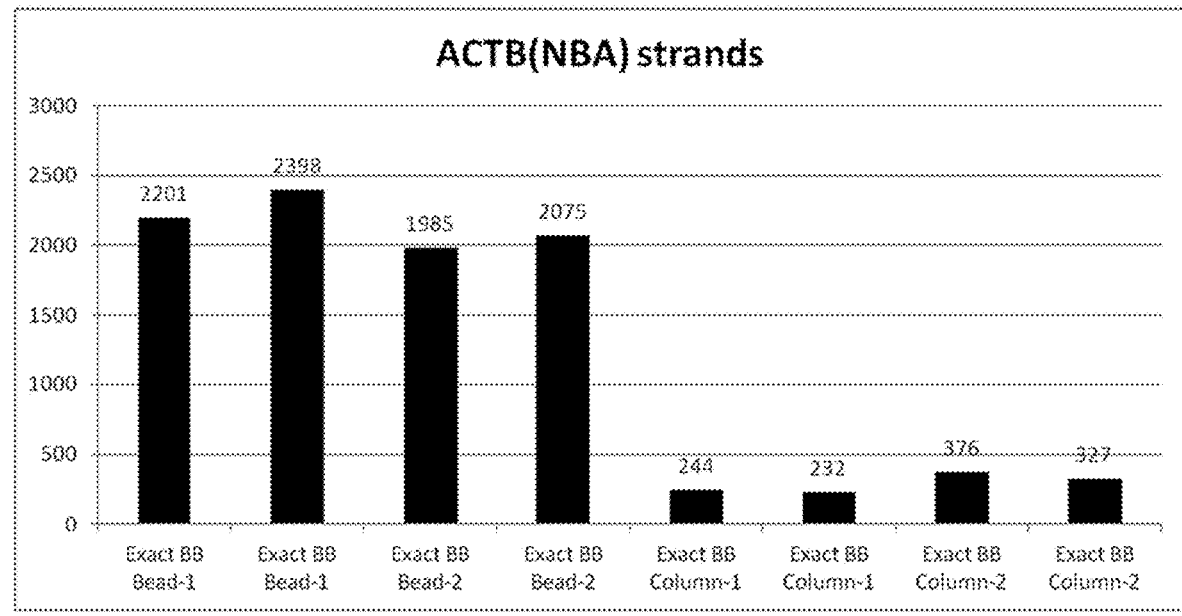

Experiments were performed to compare methods for quantifying methylation of DNA. DNA from the beta-actin (ACTB) gene was used as the input of methylated DNA for these experiments. The DNA samples were sulfonated according to the ammonium hydrogen sulfite method described above in the Methods, and the samples were subsequently desulfonated and purified according to either the magnetic bead or spin column desulfonation methods described above in the Methods. The conditions were tested using either magnetic beads or spin columns, using the buffers and procedures described above, with each tested in four replicates. The results of this experiment are shown in FIG. 3A and a repeat of this experiment is shown in FIG. 3B. These data show that the beads produce a substantially higher signal.

Example 6

Testing an Alcohol-Free Binding Buffer

During the development of embodiments of the technology disclosed herein, experiments demonstrated that a binding buffer comprising guanidine hydrochloride and no alcohol performed better than a guanidine thiocyanate binding buffer comprising alcohol.

Materials

"Gu·HCl" binding buffer: 4.5 to 8.0 M guanidine hydrochloride. For example, to make an 8 M guanidine hydrochloride stock solution, 191 g of solid guanidine hydrochloride was dissolved in 250 ml of water and mixed at 35° C. for 30 minutes. 4.5, 5.0, 5.5, 6.0, and 8.0 M solutions of guanidine hydrochloride were made by mixing 11.25, 12.5, 13.75, 15, or 20 ml, respectively, of the 8 M guanidine hydrochloride stock solution with enough water to make 20 ml total volume. The pH of the solutions was approximately 5.5 at both ambient temperature and at 75° C.

Methods

Ammonium hydrogen sulfite conversion was performed as described above in Example 5. The desulfonation reaction using magnetic beads was performed as described above in Example 5, with the substitution of a guanidine hydrochloride binding buffer (4.5-8.0 M) for the guanidine thiocyanate binding buffer containing alcohol. The desulfonation reaction using a spin column was performed as described above in Example 5. The QUARTS assay was performed as described above for Example 5.

Experiments were performed to compare the product of the bifsulfite reaction using binding buffers of 4.5 to 8.0 M guanidine hydrochloride and magnetic beads. DNA from the beta-actin (ACTB) gene was used as the input of methylated DNA for these experiments. The DNA samples were sulfonated according to the ammonium hydrogen sulfite method described above in the Methods, and the samples were subsequently desulfonated and purified according to either the magnetic bead or spin column desulfonation methods described above in the Methods for this Example. The results of this experiment are compiled in FIG. 4.

Figure 4A:
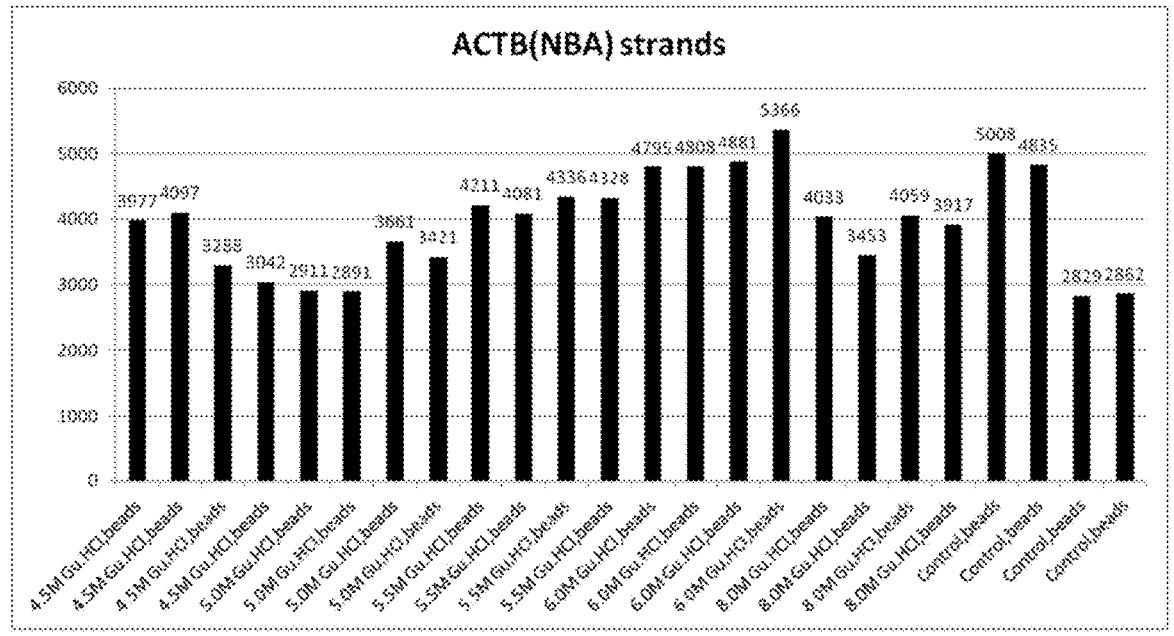
FIGS. 4A-B shows plots of data from experiments to test guanidine hydrochloride binding buffers.
Figure 4B:
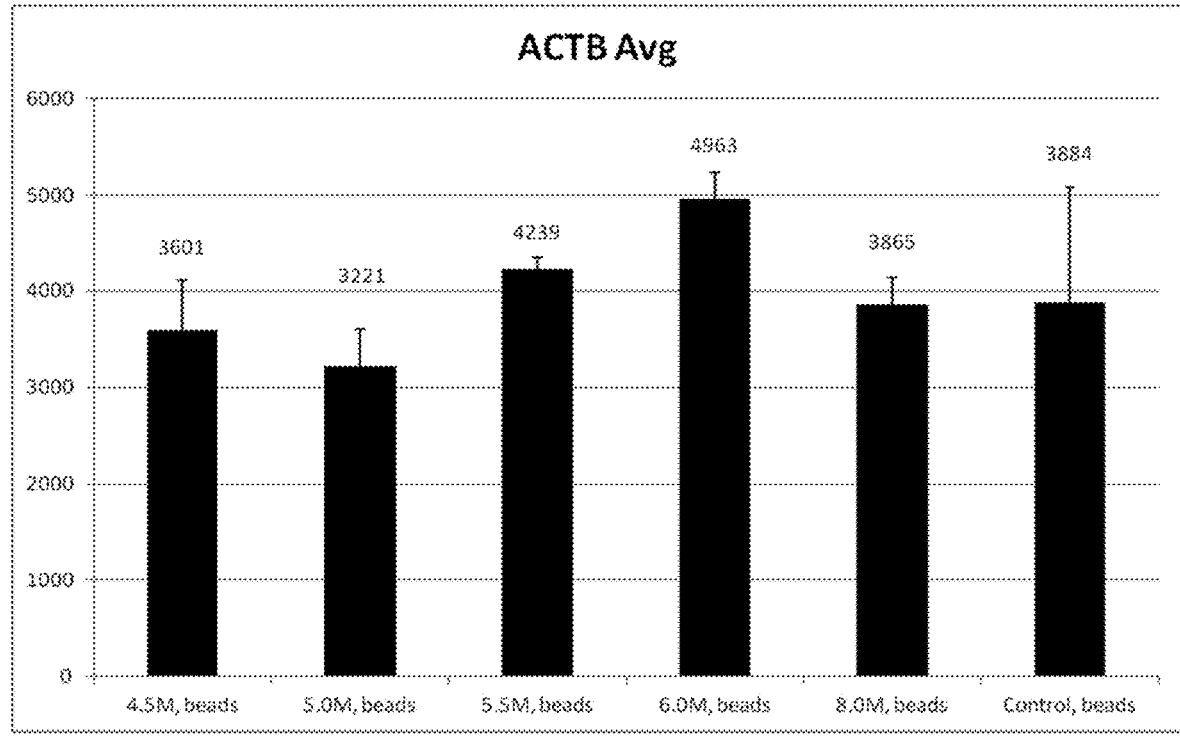

As shown in FIG. 4, a binding buffer of 6.0 M guanidine hydrochloride results in the highest quantification of DNA by QUARTS assay.

Example 7

Testing Guanidine Hydrochloride Binding Buffer

During the development of embodiments of the technology disclosed herein, experiments demonstrated that a binding buffer comprising guanidine hydrochloride and no alcohol performed better than a guanidine thiocyanate binding buffer comprising alcohol.

Materials

"Gu·HCl" binding buffers: 5.5 to 7.0 M guanidine hydrochloride. 5.5, 6.0, 6.5, and 7.0 M solutions of guanidine hydrochloride were made by mixing 13.75, 15, 16.25, or 17.5 ml, respectively, of the 8 M guanidine hydrochloride stock solution as described above with enough water to make 20 ml total volume. The pH of the solutions was approximately 5.5 at both ambient temperature and at 75° C.

Methods

Ammonium hydrogen sulfite conversion was performed as described above for Example 5. The desulfonation reaction using magnetic beads was performed as described above in Example 5 with the substitution of a guanidine hydrochloride binding buffer (5.5-7.0 M) for the guanidine thiocyanate binding buffer containing alcohol. The desulfonation reaction using a spin column was performed as described above in Example 5. The QUARTS assay was performed as described above for Example 5.

Experiments were performed to compare the product of the bifsulfite reaction using binding buffers of 5.5 to 7.0 M guanidine hydrochloride and magnetic beads to the same binding buffer. DNA from the beta-actin (ACTB) gene was used as the input of methylated DNA for these experiments. The DNA samples were sulfonated according to the ammonium hydrogen sulfite method described above in the Methods, and the samples were subsequently desulfonated and purified according to either the magnetic bead or spin column desulfonation methods described above in the Methods for this Example. The results of this experiment are compiled in FIG. 5.

Figure 5A:
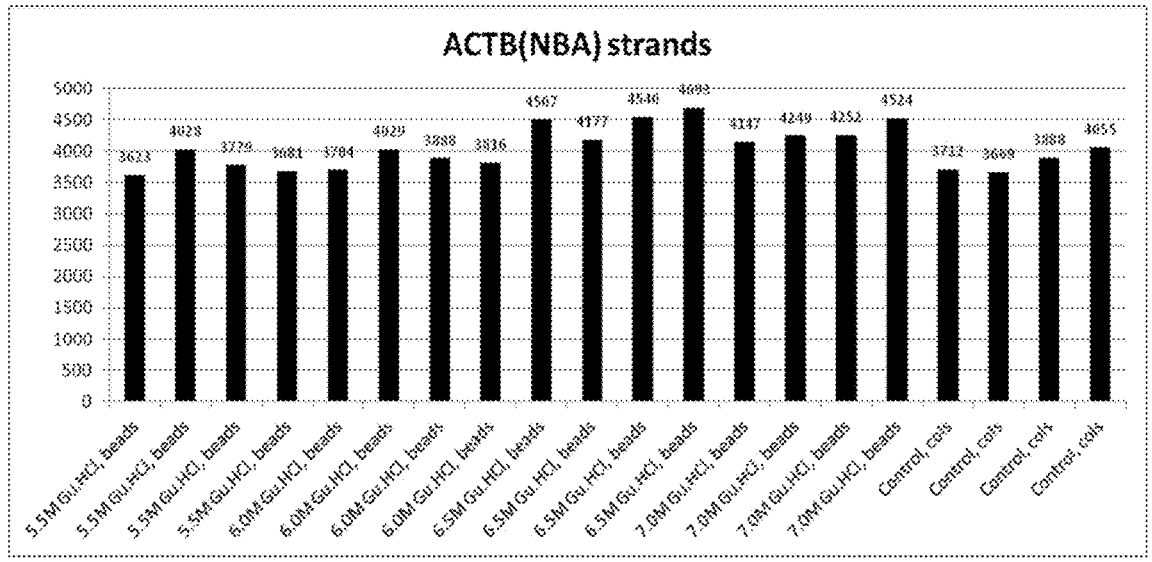
FIGS. 5A-B shows plots of data from experiments to test guanidine hydrochloride binding buffers.
Figure 5B:
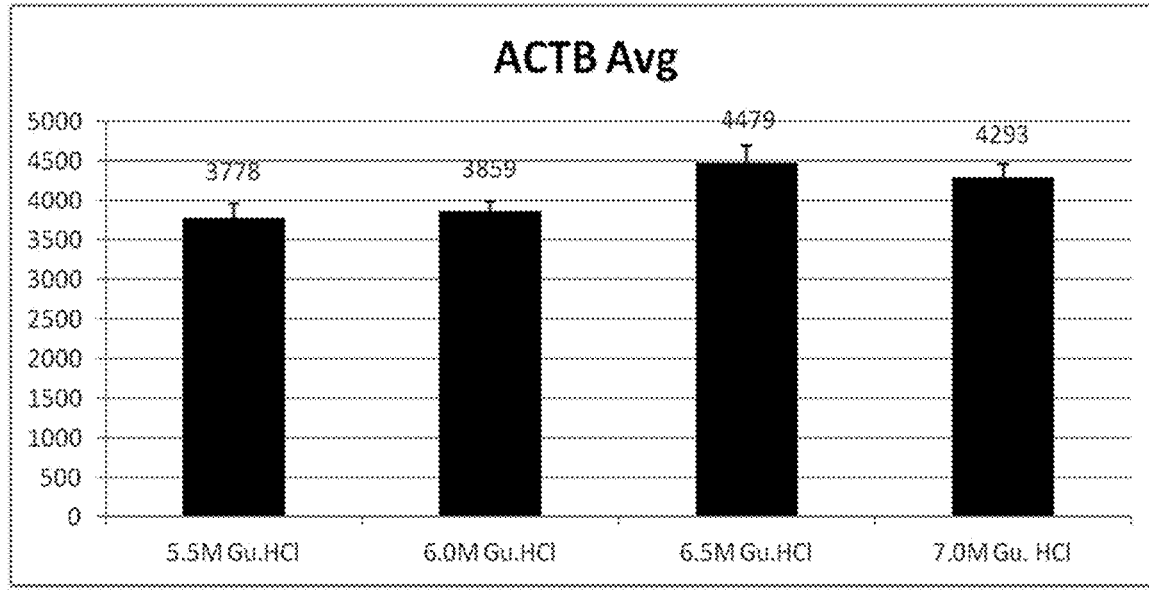

As shown in FIG. 5, a binding buffer of 6.5-7.0 M guanidine hydrochloride results in the highest quantification of DNA by QUARTS assay.

Example 8

Testing an Isopropanol Desulfonation Buffer

During the development of embodiments of the technology disclosed herein, experiments were performed to test a solution of isopropyl alcohol and sodium hydroxide (NaOH) for desulfonation reactions on silica coated magnetic particles. In particular, data were collected in experiments comparing desulfonation buffers comprising isopropanol/sodium hydroxide with conventional desulfonation buffers comprising ethanol/sodium hydroxide.

Initial experiments for silica beads purification employed a M-desulfonation buffer from the EZ-DNA Methylation™ Kit (Zymo research, PN D5002-5). In accordance with conventional methods (see, e.g., Laird, C. D., et al. (2004) "Hairpin-bisulfite PCR: Assessing Epigenetic Methylation Patterns on Complementary Strands of Individual DNA Molecules". *Proc. Natl. Acad. Sci. USA* 101: 204-209), a 0.3-N sodium hydroxide solution in 70% ethanol was initially chosen to be tested against the commercial M-Desulfonation Buffer. Experiments were performed to compare the conversion, purification, and desulfonatation of ACTB strands on beads using the M-Desulfonation Buffer and the 0.3-N NaOH solution in 70% ethanol. The data collected showed an equivalent performance between the two buffers (Table 1). Table 1 shows ACTB stand recovery after bisulfite treatment using varying desulfonation buffer formulations. The input DNA is 10 µl of captured sDNA converted with 170 µl of 68% ammonium bisulfite at 65° C. for 1 hour.

TABLE 1

| Desulfonation Buffer | Average ACTB strands (N = 2) |
|---|---|
| M-Desulfonation Buffer | 1,288 ± 46 |
| 0.3N NaOH in 70% EtOH | 1,248 ± 17 |

Figure 6:
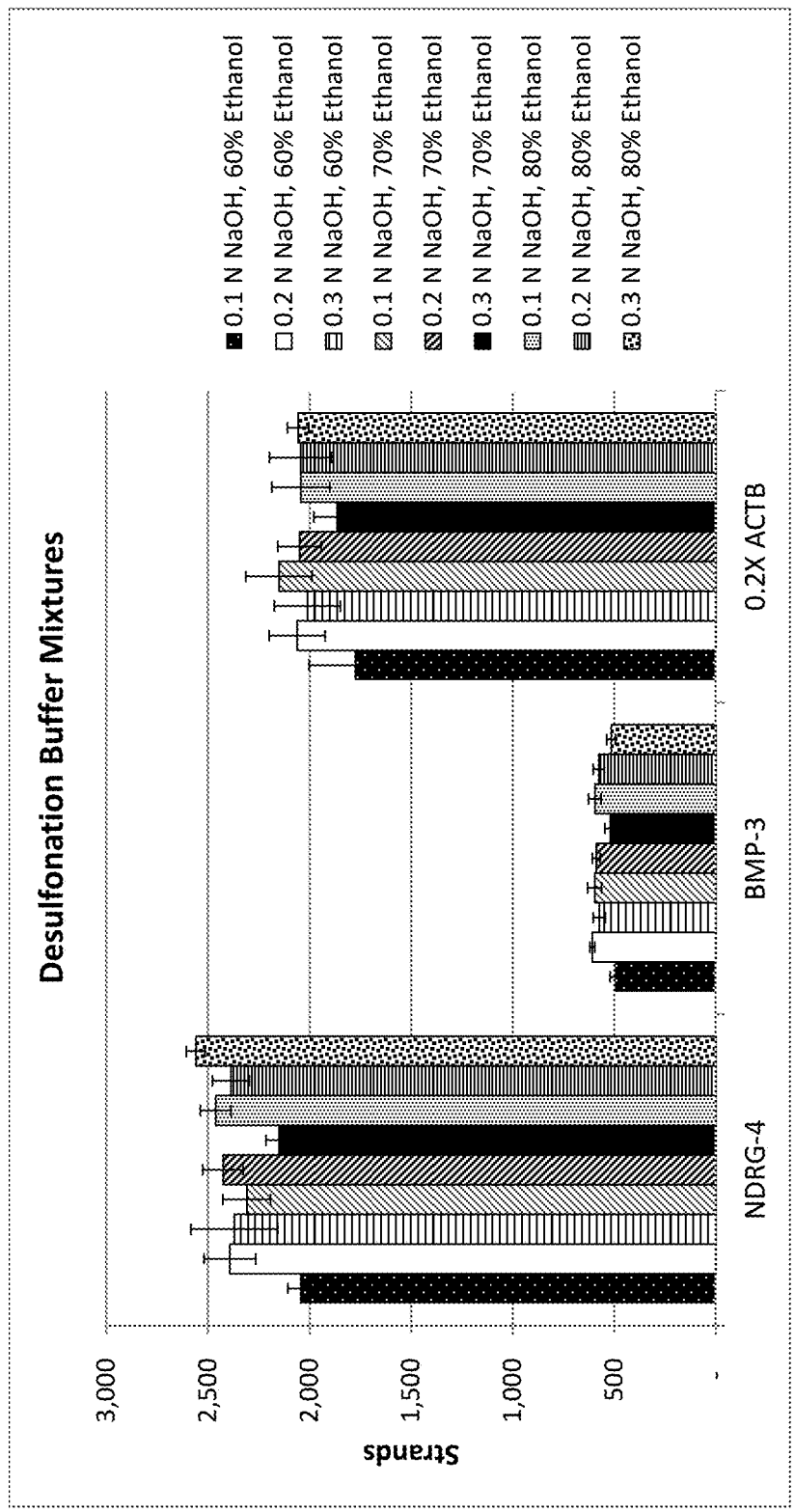
FIG. 6 shows a plot of data from experiments testing NaOH and ethanol concentrations in the desulfonation buffer. The results shown are averages of duplicate runs of a positive pool of stool DNA (sDNA) that was converted with 34% ABS at 68° C. for 1 hour followed by silica bead purification and desulfonation. In each group of bars, the order of the bars from left to right is the same as in the legend from top to bottom.

As a result of these experiments, additional experiments were performed to test the NaOH and ethanol concentrations in the desulfonation buffer. To test various amounts of ethanol and sodium hydroxide in the desulfonation buffer, experiments were performed using a positive pool of sDNA that was treated with 34% ammonium bisulfite for 1 hour at 68° C. and then bead purified and desulfonated using a series of buffers of 0.1, 0.2, and 0.3 N NaOH and 60%, 70%, and 80% ethanol. Results of this experiment showed that all buffers tested performed equal and are within experimental deviation of each other (FIG. 6). Based on these results, it was decided to use 0.3 N NaOH in 80% ethanol as the desulfonation buffer.

Figure 7:
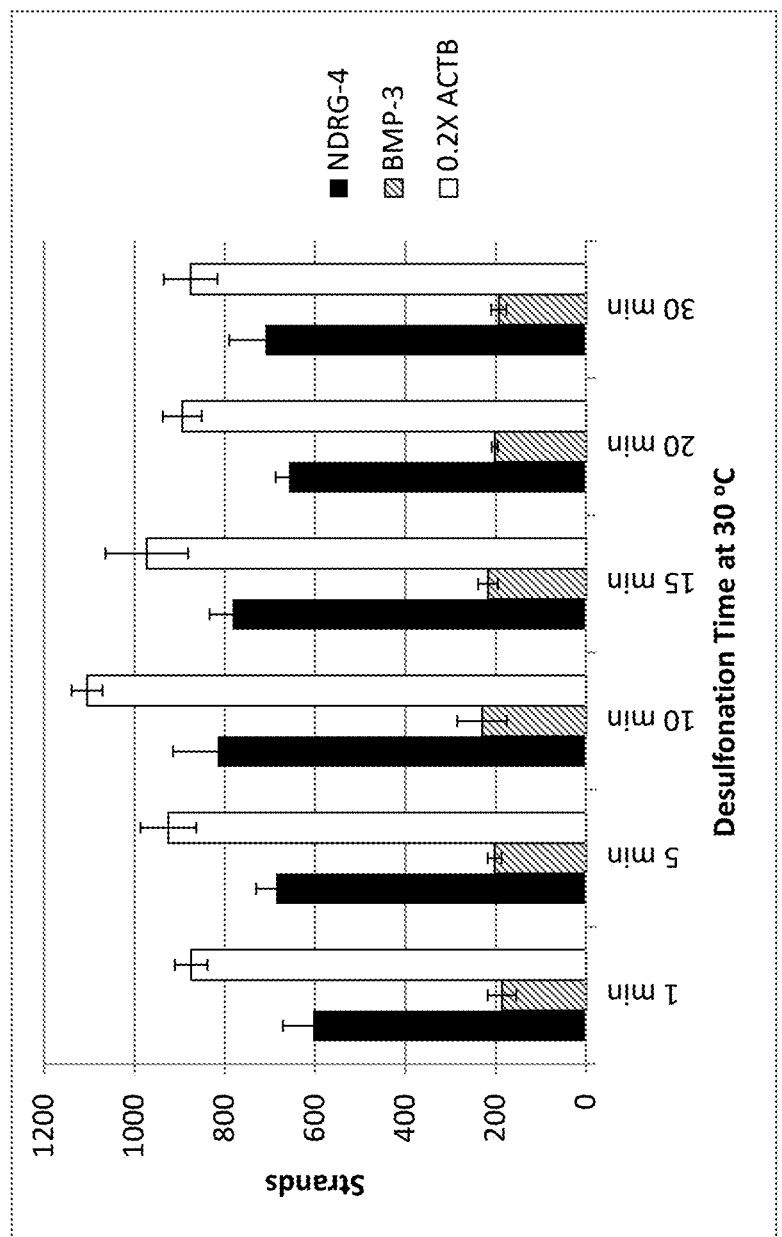
FIG. 7 shows a plot of data from experiments to evaluate desulfonation time. The results shown are averages of duplicate runs of a positive pool of sDNA converted with 34% ABS at 68° C. for 1 hour followed by silica bead purification and desulfonation. In each group of bars, the order of the bars from left to right is the same as in the legend from top to bottom.

Further experiments were conducted to test various incubation times for the desulfonation reaction. These experiments used a positive pool of sDNA that was treated with 34% ammonium bisulfite for 1 hour at 68° C., then bead purified and desulfonated using 0.3 N NaOH and 80% ethanol for various times. Results show that 10 minutes of desulfonation time is sufficient for the reaction (FIG. 7).

During the development of embodiments of the technology provided herein, experiments demonstrated that a desulfonation reagent comprising sodium hydroxide and ethanol produced a white precipitate after being exposed to air for more than approximately one hour. For example, ongoing experiments using the 80% ethanol, 0.3-N NaOH desulfonation buffer showed that its prolonged exposure to air caused the formation of a white precipitate, most likely sodium carbonate, that does not dissolve readily. In further testing of various ethanol and NaOH concentrations for desulfonation and precipitation, reagents ranging from 70% to 90% ethanol and 0.1 to 0.3 N NaOH formed a white precipitate within 3 hours of air exposure. Such a precipitate could cause problems and/or assay errors in some embodiments of the technology in which steps are integrated into an automated workflow. As result, alternative desulfonation buffer compositions were tested.

Experiments were conducted to test alternative desulfonation buffers as possible replacements of the conventional ethanol-based buffers. The experiments described below demonstrated that the use of isopropyl alcohol instead of ethanol minimized or eliminated the precipitate formation problem.

Various desulfonation solutions comprising isopropyl alcohol as a replacement for ethanol were made and tested by placing them in open containers for 3 hours to determine if a precipitate formed. Initial observations were that upon mixing of the solution, certain isopropyl alcohol/NaOH solutions did not form a precipitate but rather formed a distinct bilayer. Table 2 lists the various isopropyl alcohol desulfonation buffers made and their propensity to form a distinct bilayer.

TABLE 2

Isopropyl alcohol and sodium hydroxide buffers tested

| % isopropyl alcohol | NaOH, (N) | Bilayer formation |
|---|---|---|
| 90% | 0.3N | Yes |
| 90% | 0.2N | Yes |
| 90% | 0.1N | Yes |
| 80% | 0.3N | Yes |
| 80% | 0.2N | Yes |
| 80% | 0.1N | Yes, Moderate |
| 70% | 0.3N | Yes |
| 70% | 0.2N | Yes, Moderate |
| 70% | 0.1N | No |

As a result of testing solutions comprising isopropyl alcohol and sodium hydroxide for precipitation, further experiments were conducted to test buffers comprising 70% isopropyl alcohol and 0.1 N NaOH for desulfonation activity. Comparing the performance of a buffer comprising 80% ethanol/0.3 N NaOH versus a buffer comprising 70% isopropyl alcohol/0.1 N NaOH on high and low levels ("HD" and "LD," respectively) of converted synthetic strands showed that the use of 70% isopropyl alcohol results in slightly better strand conversion than ethanol (Table 3).

For these experiments, HD and LD ultramers (chemically synthesized strands of approximately 150 to 200 nucleotides) were used. 200 µl of HD ultramers contained $1.7 \times 10^5$ strands of each of the synthetic methylated NDRG and BMP3 target DNAs and $2 \times 10^6$ strands of each of the ACTB and KRAS targets. LD ultramers contained $5 \times 10^4$ strands of each of the synthetic methylated NDRG and BMP3 and $2 \times 10^6$ strands of each of the synthetic ACTB and KRAS. Ultramers that went through ABS conversion and are in 34% ABS solution were mixed with 750 µl of 7 M guanidine HCl and 50 µl of 16 µg/µl silica beads and allowed to bind while mixing at 1,000 rpm for 30 minutes. Beads were then washed two times, desulfonated for 10 minutes using 70% isopropyl alcohol/0.1 N NaOH or 80% ethanol (EtOH)/0.3 N NaOH desulfonation buffer at 30° C., washed twice, and dried at 75° C. for 15 minutes followed by elution with 70 µl. In Table 3, average strands and standard deviations are the result of 23 replicates.

TABLE 3

Isopropyl alcohol-based versus ethanol-based desulfonation buffers

| Methylation Marker | | NDRG4 | | BMP3 | | ACTB | |
|---|---|---|---|---|---|---|---|
| Desulfonation Buffer | | EtOH | IPA | EtOH | IPA | EtOH | IPA |
| HD Ultramers | Average Strands | 565 | 904 | 349 | 570 | 5,337 | 8,594 |
| | Standard Deviations | 148 | 129 | 82 | 101 | 1,445 | 1,546 |
| LD Ultramers | Average Strands | 128 | 260 | 82 | 137 | 4,359 | 7,908 |
| | Standard Deviations | 44 | 41 | 19 | 33 | 1,193 | 929 |

To test the effect of changing the desulfonation time for reactions using the 70% IPA, 0.1 N NaOH buffer, experiments were performed using a pool of positive sDNA to compare desulfonation times of 5, 10, 20, and 30 minutes at 30° C. In the experiments, 200 μl of converted sDNA in 34% ABS solution were mixed with 750 μl of 7 M guanidine HCl and 50 μl of 16 μg/μl silica beads and allowed to bind while mixing at 1,000 rpm for 30 minutes. Beads were then wash two times, desulfonated for various times using 70% isopropyl alcohol, 0.1 N NaOH at 30° C., washed twice, and dried at 75° C. for 15 minutes followed by elution with 70 μl. Average strands and coefficients of variation are the result of three replicates.

Results show that 10 minutes of desulfonation is sufficient and that more desulfonation time does not result in significantly higher strand desulfonation (Table 4).

TABLE 4

Testing desulfonation time using a desulfonation buffer of 70% IPA, 0.1 N NaOH

| Desulfonation Time | Average Strands (N = 3) | | | % CV | | |
|---|---|---|---|---|---|---|
| | NDRG4 | BMP3 | ACTB | NDRG4 | BMP3 | ACTB |
| 5 minutes | 2,668 | 920 | 10,788 | 15% | 13% | 14% |
| 10 minutes | 3,084 | 1,029 | 12,245 | 11% | 9% | 13% |
| 20 minutes | 3,141 | 1,012 | 12,089 | 5% | 5% | 6% |
| 30 minutes | 3,477 | 1,112 | 12,868 | 6% | 5% | 10% |

Further experiments were conducted to test various reaction conditions by assessing the effect of minor formulation deviations on the effectiveness of the desulfonation buffer. In these experiments, various formulations deviating slightly from the 70% IPA, 0.1 N NaOH buffer were made and tested. A volume of 200 μl of converted sDNA in 34% ABS solution were mixed with 750 μl of 7 M guanidine HCl and 50 μl of 16 μg/μl silica beads and allowed to bind while mixing at 1,000 rpm for 30 minutes. Beads were then washed two times, desulfonated for 10 minutes using the indicated desulfonation buffer at 30° C., washed twice, and dried at 75° C. for 15 minutes followed by elution with 70 μl. Average strands and coefficients of variation are the result of three replicates. Minor fluctuations in the isopropyl alcohol or NaOH concentrations have negligible effects on the desulfonation efficiency (Table 5).

TABLE 5

Assessment of minor formulation deviations on desulfonation buffer effectiveness

| Desulfonation Buffer | Average Strands (N = 3) | | | % CV | | |
|---|---|---|---|---|---|---|
| | NDRG4 | BMP3 | ACTB | NDRG4 | BMP3 | ACTB |
| 70% IPA, 0.1 N NaOH (Control) | 11,121 | 3,663 | 54,250 | 1% | 4% | 3% |
| 70% IPA, 0.125 N NaOH | 11,092 | 3,679 | 56,262 | 5% | 7% | 8% |
| 70% IPA, 0.075 N NaOH | 12,607 | 4,147 | 63,329 | 5% | 5% | 8% |
| 60% IPA, 0.1 N NaOH | 10,526 | 3,520 | 52,178 | 2% | 3% | 3% |
| 65% IPA, 0.1 N NaOH | 11,641 | 3,804 | 56,618 | 11% | 10% | 12% |

Based on these results, a formulation of 70% isopropyl alcohol, 0.1 N NaOH was selected for the desulfonation buffer.

Example 9

Protein Solutions to Improve Nucleic Acid Recovery

During the development of embodiments of the technology disclosed herein, data were collected that demonstrated significant variation in the recovery of DNA (e.g., bisulfite-treated DNA) from capture probes in reaction vessels. The variation observed on reaction plates (e.g., multiwall plates such as 96-deep well plates) appeared to be a function of well location in the plate. In particular, it was demonstrated that the recovery of DNA varied top-to-bottom (e.g., as a function of plate row) and/or left-to-right (e.g., as a function of plate column). In some experiments, the variation was as much as threefold. For example, experiments using replicated samples of a target nucleic acid (e.g., NDRG4) across an entire plate showed that the number of strands recovered from the different wells on the plate varied in general from the top (row A) to the bottom (row H) of a 96-well plate (see, e.g., FIG. 8).

Variation in recovery efficiency associated with particular positions on a sample plate is prohibitive to adapting the technology to an automated, high-throughput format (e.g., on a multi-well plate such as a 96 deep-well plate). Attempts to resolve this issue included experiments performed using multi-well plates sourced from different manufacturers, changing the order of reagent addition, washing the plates before use (e.g., with NaOH). None of these trials successfully reduced the variation in strand recovery.

Further experiments were performed to test the effect of adding proteins, e.g., bovine serum albumin (BSA) or casein, to solutions used to wash captured DNA on the plate or to elute DNA from the capture probes, as described herein. As discussed below, these tests showed that BSA and casein reduced or eliminated the aberrations in strand recovery in the multi-well plates. In some embodiments, the BSA and/or casein is added to the wash solution used after the capture step and before the high-pH elution step.

In some embodiments, the DNA is bisulfate-treated DNA. Experiments demonstrated that addition of BSA to a final concentration of about 10 ng/µl reduced the variation in recovery observed for bisulfate-treated panel of ACTB, NDRG-4, and BMP-3 ("ANB" panel).

For example, in some experiments, the variation was reduced from approximately a threefold difference between the top and the bottom of the plate to no difference or to approximately a relative ratio of 1.25 between the top and the bottom of the plate. See, e.g., FIG. 10, which compares the effects of different concentrations of BSA on the recovery of NDRG4 and KRAS 38A DNA. The data in FIG. 10 shows replicates of methylation assay NDRG-4 strands (columns 2-5) and mutation assay KRAS 38A strands (columns 8-11). For the methylation assay, a 4 times increase in average strands is observed upon addition of BSA, and further shows that the addition of BSA decreased the trending down the plate from 3-fold as shown in FIG. 9, to 1.25-fold, as observed by dividing average strands of rows H by row A in FIG. 10.

This reduction in variation was from approximately 300% to 30%. Further experiments to test BSA concentrations showed that BSA alleviated the observed variation at a BSA concentration of approximately 27 ng/µl or more and, moreover, and that strand recovery was increased with increasing BSA concentrations up to approximately 100 ng/µl, as shown below:

| | ng/µL | Avg Strands | | % CV | |
|---|---|---|---|---|---|
| | BSA | ANB | KRAS | ANB | KRAS |
| FAM | 28 | 6960 | 21460 | 19% | 21% |
| | 55 | 7296 | 24928 | 15% | 18% |
| | 900 | 6738 | 31856 | 11% | 16% |
| | 1800 | 4383 | 26150 | 11% | 26% |
| HEX | 250 | 3146 | 14423 | 16% | 17% |
| | 500 | 3189 | 18379 | 11% | 13% |
| | 900 | 3443 | 23000 | 11% | 16% |
| | 1800 | 2280 | 20319 | 6% | 17% |
| QSR | 250 | 64815 | 120769 | 18% | 20% |
| | 500 | 80171 | 125977 | 18% | 14% |
| | 900 | 70401 | 163284 | 15% | 13% |
| | 1800 | 56421 | 143850 | 9% | 12% |

The panels and fluorophores are as described for FIG. 11. These data are averaged signals for 46 QUARTS assay reactions.

In other experiments performed to test the effect of casein in alleviating the observed variation, data collected demonstrated that adding casein, e.g., alkaline denatured casein, to one or more solutions at a concentration of 0.001% to 0.01% (e.g., comparing 0.001%, 0.003%, 0.006%, and 0.01%) reduced or eliminated the variation of DNA strand recovery with well position and an increased DNA strand recovery was observed with increased casein concentration. In some experiments directly comparing the effects of BSA and casein, data showed that casein doubles strand recovery compared to BSA. See, e.g., FIG. 11. Additional experiments demonstrated that pre-washing and rinsing the multi-well plates with a BSA solution (e.g., prior to DNA capture) also decreased the variation.

In some experiments, this problem of DNA strand recovery varying as a function of well position in a multi-well plate was associated with processing (e.g., bisulfite conversion and/or purification, elution) of DNA of approximately 200 nucleotides or less in a multi-well format (e.g., in a deep-well plate such as a 96 deep-well plate). As this phenomenon was unexpected, the physical basis of the systematic variation is not known and the mechanism of minimizing or eliminating the variation by BSA and/or casein is not known. However, an understanding of the basis for the variation and/or the mechanism by which it is minimized or eliminated by BSA and/or casein is not required to practice the technology. Without being bound by theory, one explanation may be that the BSA and/or casein minimizes or eliminates the binding of DNA to well surfaces that vary, e.g., due to the manufacturing process and/or defects in the plates.

In summary, during the development of embodiments of the technology related to automation integration (e.g., performing capture, washing, elution, conversion, and purification on an automated instrument and 96 deep-well format), a systematic (e.g., top-to-bottom, left-to-right) trending pattern of varying strand recovery (e.g., up to approximately threefold) from capture probes was observed for strands of DNA (e.g., bisulfite-converted synthetic DNA). Various solutions were tested and data suggested that the addition of BSA or casein minimized or eliminated variation in DNA strand recovery and increased recovery of DNA strands, e.g., eluted from capture probes.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in biochemistry, molecular biology, clinical medicine, genomics, or related fields are intended to be within the scope of the following claims.

We claim:

1. A system comprising:
   a) a composition comprising:
      i) single-stranded small DNA comprising sulfonated cytosine deoxynucleotides, wherein the small DNA is 200 or fewer nucleotides in length, and wherein the small DNA is bound to silica or silica-coated beads, in a mixture with
      ii) an alcohol-free solution comprising ammonium hydrogen sulfite and 5.5 to 7.5 M guanidine hydrochloride;
   b) a desulfonation reagent comprising NaOH and isopropanol; and
   c) a wash buffer comprising ethanol.

2. The system of claim 1, further comprising a solution comprising at least one of bovine serum albumin and/or casein.

3. The system of claim 2, wherein the solution comprises between 10 ng/µl and 100 ng/µl bovine serum albumin.

4. The system of claim 2, wherein the solution comprises between 0.001% to about 0.01% casein.

5. The system of claim 1, wherein the alcohol-free solution comprises 6.5-7.0 M guanidine hydrochloride.

6. The system of claim 1, wherein the alcohol-free solution comprises 7.0 M guanidine hydrochloride.

7. The system of claim 1, wherein the desulfonation reagent comprises 60% to 70% isopropanol.

8. The system of claim 1, wherein the desulfonation reagent comprises 70% isopropanol.

9. The system of claim 1, wherein the desulfonation reagent comprises 0.075 to 0.125 N sodium hydroxide.

10. The system of claim 1, wherein the desulfonation reagent comprises 0.1 N sodium hydroxide.

11. The system of claim 1, wherein the silica-coated beads are magnetic.

12. The system of claim 11, further comprising a magnet.

13. The system of claim 1, wherein the composition comprises 6.6 to 6.8% ammonium hydrogen sulfite.

* * * * *